US009655692B2

United States Patent
Lucas

(10) Patent No.: US 9,655,692 B2
(45) Date of Patent: May 23, 2017

(54) PRE-FABRICATED ANTERIOR GUIDANCE PACKAGE KIT FOR PATIENTS HAVING BRUXISM/CLENCHING HABIT WITH OR WITHOUT VARIOUS MALOCCLUSIONS-II

(71) Applicant: Kelly Wade Lucas, Wasilla, AK (US)

(72) Inventor: Kelly Wade Lucas, Wasilla, AK (US)

( * ) Notice: Subject to any disclaimer, the term of this patent is extended or adjusted under 35 U.S.C. 154(b) by 363 days.

(21) Appl. No.: 14/083,467

(22) Filed: Nov. 19, 2013

(65) Prior Publication Data

US 2015/0136147 A1    May 21, 2015

(51) Int. Cl.
*A61C 7/08* (2006.01)
*A61C 7/36* (2006.01)

(52) U.S. Cl.
CPC . *A61C 7/08* (2013.01); *A61C 7/36* (2013.01)

(58) Field of Classification Search
CPC     A61C 7/08; A61C 7/36; A63B 71/085; A61F 5/566
USPC .................................................. 128/859–862
See application file for complete search history.

(56) References Cited

U.S. PATENT DOCUMENTS

| | | | |
|---|---|---|---|
| 2,529,429 A | 11/1950 | Spiro | |
| 4,773,854 A | 9/1988 | Weber | |
| 4,901,737 A | 2/1990 | Toone | |
| 5,059,120 A | 10/1991 | Lee | |
| 5,085,584 A | 2/1992 | Boyd | |
| 5,203,701 A * | 4/1993 | Burtch | A61F 5/01 433/215 |
| 5,365,945 A | 11/1994 | Halstrom | |
| 5,427,117 A | 6/1995 | Thornton | |
| 5,722,828 A | 3/1998 | Halstrom | |
| 5,795,150 A | 8/1998 | Boyd | |

(Continued)

FOREIGN PATENT DOCUMENTS

EP        0312368        12/1993

OTHER PUBLICATIONS http://www.greatlakesortho.com/content/files/resources/SplintApplianceSelectionGuide_S222.pdf. Frank., et al.

(Continued)

*Primary Examiner* — Kari Rodriquez
(74) *Attorney, Agent, or Firm* — Troutman Sanders LLP; Ryan A. Schneider; Brennan M. Carmody

(57) ABSTRACT

A pre-fabricated, pre-programmed or custom-made guidance package is provided. The Anterior Guidance Package (AGP) of current invention is comprised of one maxillary guidance component and one mandibular guidance component produced in many shapes and sizes. Those components are attached to a maxillary retention piece and a mandibular retention piece, respectively when the mandible is at a point defined by an operator to provide ideal anterior guidance for the mandible, or to provide specialized guidance for a damaged stomatognathic system. In contrast to all current bruxism or Tempor-mandibular disorders (TMD) appliances, the AGP according to current invention provides a wide range of features and options including three-dimensional control, superior mechanical advantage and preferable vertical dimension at rest. The primary purpose is to provide a superior anterior guidance night guard including relief of centric occlusion/centric relation discrepancy for the amelioration of the damage and pain caused by bruxism.

12 Claims, 22 Drawing Sheets

(56) References Cited

U.S. PATENT DOCUMENTS

| | | |
|---|---|---|
| 5,868,138 A | 2/1999 | Halstrom |
| 6,041,784 A | 3/2000 | Halstrom |
| 6,161,542 A | 12/2000 | Halstrom |
| 6,666,212 B2 | 12/2003 | Boyd, Sr. |
| 6,886,566 B2 | 5/2005 | Eubank |
| 7,556,044 B2 | 7/2009 | Ball |
| 7,654,267 B2 | 2/2010 | Boyd |
| 8,156,940 B2 | 4/2012 | Lee |
| 2002/0000230 A1 | 1/2002 | Gaskell |
| 2005/0288624 A1 | 12/2005 | Boyd |
| 2007/0079833 A1 | 4/2007 | Lamberg |
| 2007/0099144 A1 | 5/2007 | Keski-Nisula |
| 2007/0178420 A1 | 8/2007 | Keski-Nisula |
| 2008/0000483 A1 | 1/2008 | Halstrom |
| 2008/0099029 A1 | 5/2008 | Lamberg |
| 2010/0147315 A1 | 6/2010 | Chodorow |
| 2010/0279246 A1 | 11/2010 | Keski-Nisula |
| 2011/0030704 A1 | 2/2011 | Hanna |
| 2011/0114100 A1 | 5/2011 | Alvarez |
| 2011/0132380 A1* | 6/2011 | Goldsby ............ A61B 1/24 128/861 |
| 2011/0139162 A1 | 6/2011 | Chodorow |
| 2011/0308532 A1 | 12/2011 | Nelissen |
| 2012/0266896 A1 | 10/2012 | Chodorow |
| 2012/0266897 A1 | 10/2012 | Chodorow |
| 2012/0272972 A1 | 11/2012 | Chodorow |
| 2013/0098375 A1 | 4/2013 | Urbanek |
| 2013/0146067 A1 | 6/2013 | Tschackert |

OTHER PUBLICATIONS http://www.chairsideSplint.com.

Laura Maestre-Ferrin, et al., "Virtual articulator for the analysis of dental occlusion: An update," Med Oral Patol Oral Cir Bucal. vol. 17(1): e160-a163, Jan. 2012.

E. Solaberrieta, et al., "Design of a Virtual Articulator for the Simulation and Analysis of Mandibular Moments in Dental CAD/CAM," Proceedings of the 19th CIRP Design Conference-Competitive Design, pp. 323, 30-31, Mar. 2009.

Frank, et al., "Great Lakes Digital Splint," http://www.greatlakesortho.com/resource-center/digital-splints-users-group.

* cited by examiner

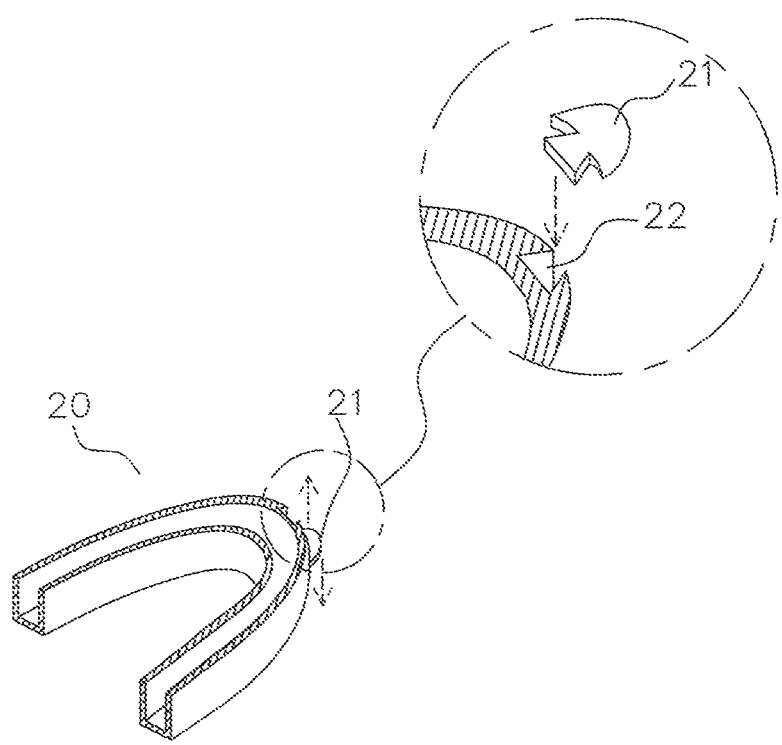
FIG. 16-b

PRE-FABRICATED ANTERIOR GUIDANCE PACKAGE KIT FOR PATIENTS HAVING BRUXISM/CLENCHING HABIT WITH OR WITHOUT VARIOUS MALOCCLUSIONS-II

Current application is Continue-in Part of U.S. patent application Ser. No. 13/573,283, which was filed on Sep. 6, 2012.

FIELD OF THE INVENTION

Current application relates to an anterior guidance package, especially an anterior guidance package pre-fabricated in various sizes and shapes to be used to produce a superior night guard for the amelioration of the damage and pain caused by bruxism, or the treatment of other various maladies of the stomatognathic system to include the mouth, jaw, muscles or other tissues of mastication, or the TMJ.

BACKGROUND OF THE INVENTION

Bruxism is an inappropriate activity that causes many dental and medical problems. Dental conditions to include malocclusion and centric relation/centric occlusion discrepancy can amplify the damage caused by bruxism. Some of the problems include myo-facial pain syndrome, damage to teeth, and damage to the temporo-mandibular joints (TMJ). Many kinds of 'night guards' have been developed to ameliorate the negative impacts of bruxism. These include appliances that provide simple coverage of teeth, and also appliances that correct the centric relation/centric occlusion discrepancy which allow the TMJ to relax in its most anatomically appropriate and best stress bearing position (centric relation), and also appliances that provide anterior guidance, which among other benefits reduces significantly the inappropriate muscle force associated with bruxism. The best night guards are those that combine all three of these features. Simple coverage of teeth does help reduce damage to teeth by providing a barrier. However, without centric occlusion/centric relation (CO/CR) discrepancy correction and without anterior guidance, this type of night guard could actually cause increased severity of bruxism. As a result, causes worse myo-facial pain syndrome and a greater tendency toward TMJ damage. The correction of a centric occlusion/centric relation (CO/CR) discrepancy eliminates deviating tooth contacts in the posterior occlusion allowing the condyles to seat into their most comfortable positions. By eliminating the contact of deviating inclines of teeth in a malocclusion there will be no proprioceptive message to muscles to deviate around that interference. When the muscle stops being stimulated into holding the mandible in a deviated position, then normal muscle activity can resume and spasticity will cease. Anterior guidance refers to a particular function of anterior teeth to provide physical limits of movement of the front end of the mandible. Appropriate anterior guidance in centric relation position, long centric, straight protrusive and lateral excursions protects back teeth and reduces the muscle forces of bruxism because of the mechanical advantageous position of being anterior to the muscle power used to close the mandible. Traditionally, dentists have been able to improve CO/CR discrepancies and anterior guidance by creating a custom made and custom adjusted night guard, which typically are attached to the maxillary or mandibular teeth and opposed by natural teeth. This appliance is custom built for a patient by a dentist considering their particular malocclusion and other factors allowing the mandible to be in centric relation with appropriate anterior guidance giving the patient significant relief from the damage and pain of bruxism. However, a dentist must spend a lot of time and effort to custom create and custom modify a night guard to try to achieve appropriate anterior guidance and reduce CO/CR discrepancy for a patient's particular malocclusion. These efforts are further complicated by missing teeth, or periodontally weakened teeth. The patient must also spend a lot of time to achieve the desired result and a high cost. It is the purpose of the current invention to provide a means to allow a dentist or even a non-dentist to create a superior night guard that is easier and faster to make and more affordable for the patient. It is another purpose of the current invention to remove the variable factors of maloccluded teeth, missing or periodontally weakened teeth. The third purpose of the current invention is to provide superior anterior guidance and simultaneously obliterate any CO/CR discrepancy by an individual who does not even necessarily posses the specialized knowledge of a dentist. A less common application of the current invention is to provide a treatment platform for other maladies of mouth, jaw, muscles or other tissues of mastication, or the TMJ (temporomandibular joint). The three-dimensional guidance and limits for the mandible available with the current invention allow a clinician treatment strategies heretofore not available.

DESCRIPTION OF PRIOR ARTS

U.S. Patent Application Publication 20100279246, 20070178420, 20070099144 by Keski-Nisula; Katri; et al. discloses an odontological device and device series to guide an individual's occlusion and a method to be used in selecting an occlusion guidance appliance device to be used in orthodontic treatment. This kind of device contains a U-shaped arch with a lower surface on the side of the lower jaw and a higher surface on the side of the upper jaw, and in both of which there are concaves in which to place the individual's teeth, and where the bottoms of the concaves form of the isthmus separating the concaves from one another.

United States Patent Application publication 20130146067 to Tschackert illustrates a dental splint with a U-shaped base and wall-shaped reinforcements on the tongue and lip sides, said reinforcements forming channels, and to a method for the production of said dental splint. The dental splint for the upper jaw can be designed such that a free space is formed in the front teeth region after inserting the dental splint and clenching the teeth, whereby additional air for breathing can reach the oral cavity.

United States Patent Application Publication 20130098375 to Urbanek illustrates a device for mitigation of temporomandibular joint disorder with lingual tooth surface contact surface, hard palate conformity, anterior pad, and pad wings. The device is conformed in essentially a U-shape, or arch, having an anterior middle portion. Extending posteriorly from opposite sides of the anterior middle portion are pad wings. The whole device is contoured to communicate with an upper jaw and detention thereof. The device comprises a top surface and a bottom surface.

United States Patent Application Publication 20120272972, 20120266897, 20120266896, 20110139162 and 20100147315 to CHODOROW illustrates a one-piece molded bruxism treatment device which in upright orientation has top and bottom parts, including: an elongated band having a generally U-shape defining a closed front end part and legs extending rearward and adapted to be positioned around the outer surfaces of a person's upper gums and teeth, and two generally planar resiliently deformable bite pads oriented generally horizontally, each extending from one of the feet of the band medially toward the other.

United States Patent Application Publication 20110308532 to Nelissen illustrates an apparatus which can be placed clampingly on a lower jaw or upper jaw, in particular on the molars and/or pre-molars thereof, essentially consisting of: —at least a left and a right buccal shaped body on the buccal side; —one or more connecting elements between the left and right buccal shaped body, wherein the left and right buccal shaped bodies extend at least along respectively the left and right molars and/or premolars and/or canines; and wherein the one or more connecting elements are adapted to push the left and right shaped bodies into the undercuts of the molars and/or premolars and/or canines.

United States Patent Application 20110114100 to Alvarez et al. illustrates a dental mouthpiece clenched between the teeth and used to alleviate numerous dental and medical conditions as well as increase a user's performance. The mouthpiece improves facial tone and provides relief of temporomandibular joint pain and associated grinding of the teeth. The mouthpiece is less visible than prior art devices, even when the wearer opens his/her mouth, and does not cause discomfort. Furthermore, the mouthpiece allows for substantially unaffected speech, by the strategic placement of protuberances, so that the user may keep the mouthpiece in place and proceed about his or her business without providing any sound or visual cues to the presence of the mouthpiece.

United States Patent Application 20110030704 to Hanna illustrates a comfortable multiple layer mouth protector is provided for strength and ease of fit to minimize if not completely and gradually eliminate bruxism, with spring biasing keeping the maxillary and mandibular mouth protector arches in place and apart, eliminating snoring and permitting easy breathing. In addition, this Mouth protector protects oral structures from sports injuries.

United States Patent Application 20080099029 and 20070079833 to Lamberg; Steven B. illustrates an intraoral mandibular advancement device to treat sleep disorders in a user having an obstructed airway includes a maxillary appliance with a main body for removable attachment to the maxillary teeth; a protrusive element distending from the central portion of the main body; and retention means extending from the main body for retention of the device on the maxillary teeth during sleep. A mandibular appliance removably attaches to the mandibular anterior teeth and includes a lingual spacer that extends posteriorly from the mandibular anterior teeth. The anterior aspect of the protrusive element of the maxillary appliance contacts the posterior edge of the lingual space and thereby causes mandibular advancement.

U.S. Patent Application Publication 20080000483, U.S. Pat. Nos. 6,161,542, 6,041,784, and 5,365,945 to Halstrom disclosed an intra-oral dental appliance for treatment of sleep disorders including snoring, sleep apnea and nocturnal bruxism. The appliance includes an upper member conforming to the patient's maxillary dentition; a lower member conforming to the patient's mandibular dentition; and a connecting assembly for adjustably coupling the upper and lower members together. The only benefit in regard to bruxism is that Halstrom's appliance does separate teeth therefore damage to teeth would be eliminated. However, his connecting assembly places the jaw in an unnatural position. This may cause many problems because the major goal of treatment for tooth damage, myofacial pain, migraines etc secondary to bruxism, is to allow the jaw (mandible) freedom to relax to its most comfortable position. This position would be centric relation for 99% of people. Centric relation allows the jaw to be in its most anatomically correct stress bearing position and the place where the muscles are most calm. Dentists use centric relation or this even more refined point to create a night guard that allows the mandible to rest there and then guidance from that position to avoid posterior interferences and freedom so the jaw can move, the patient can yawn, open, sneeze, breathe, swallow etc. normally.

When a person, having malocclusion, closes their mouth, the jaw is forced to adapt a position other than centric relation. Because of muscle engrams the jaw ends up living in this inappropriate position. By locking the lower jaw forward in relation to the upper jaw over time, this will happen when a person wears Halstrom's appliance, the person may experience unintended and inappropriate orthodontic movement of the teeth that create or make worse the malocclusion. By locking the lower jaw forward in relation to the upper jaw you have pulled the mandibular condyle down the articular imminence to a very inappropriate position (not in the fossa). It may prevent damage to teeth but if the person exerts muscle activity in that position one is more likely to damage the TMJ. One major purpose of a night guard is to allow the persons jaw to assume the position of centric relation, not purposely pull the jaw into some other position.

Myofacial pain would be terrible for a person wearing this type appliance since the condyles and muscles of mastication are artificially pulled into very inappropriate positions.

U.S. Patent Application Publication 20050288624, U.S. Pat. Nos. 7,654,267, 5,795,150 (which is assigned to NTUtts, Inc.), and U.S. Pat. No. 5,085,584 by Boyd, and U.S. Pat. No. 6,666,212 to Boyd. Sr., illustrate an intraoral discluder for preventing chronic tension headaches, common migraine headaches, and temporo-mandibular disorders that are caused or perpetuated by chronic activity of the temporalis muscle. The discluder includes a trough, contoured to encompass at least one maxillary or mandibular incisor, from which extends a protruding platform, for engagement by the opposing incisors. The trough can be retained on the teeth by any adaptable material than can flow around the teeth and then maintain its shape. Once in place in the wearer's mouth, one or two opposing incisors will come into contact with the platform prior to the upper and lower posterior and/or canine teeth coming into contact, regardless of the position of the mandible, thereby reducing the intensity of the activity of the temporalis muscle. In addition, a special post on the discluder's platform is engageable directly with one or more opposing incisors, to act as a stop and thereby inhibit excessive retrusive movement of the mandible and urge the mandible toward a more protrusive position. This can reduce the intensity of undesired clenching, and it can enhance the size of the wearer's pharyngeal airspace, thereby reducing the incidence and severity of snoring.

However, Boyd's invention did not consider patients who have malocclusion, loss of teeth and weak teeth, etc. If a patient with such abnormalities on teeth wears Boyd's intraoral discluder and brux while sleep and functions against these teeth, it could make the patient's tooth problems worse. Also, many people have reported chipping teeth, which oppose this appliance. Also, because the guidance is flat there are many malocclusions that to disclude the mandible enough to avoid the posterior interferences the vertical dimension of the appliance could become so big as to make the appliance uncomfortable or impossible to wear.

This appliance therefore cannot intervene as effectively to as many types and severities of malocclusions as the current invention.

On the web site of http://www.ChairsideSplint.com NTI-tts, Inc. commercially broadcast a new intraoral discluder for preventing chronic tension headaches, common migraine headaches, and temporo-mandibular disorders that are caused or perpetuated by chronic activity of the temporalis muscle. That product is shown in the U.S. Pat. No. 6,666,212 to Boyd Sr. But, NTI-tts modified the Boyd's invention slightly by developing a three dimensional guidance on the surface of the surface of the through (18) by trial and error of a dentist. They said it usually take couple of hours to finish that "opposing slider." In their video, a dentist engages a preliminary "opposing slider" on the mandibular incisors of a patient and asks the patient whether the "pain" is gone or better. If the patient say 'no', the dentist takes it out of the patient's mandibular incisors and cuts the surface of the trough (18) again and again until the patient says its 'better.' So trail and error customization by a dentist is still necessary, and is not so different from the traditional method of carving anterior guidance under the lower surface of maxillary retention piece of a traditional splint. The only difference is that the "opposing slider" is smaller and cheaper. It does not eliminate the trial and error method performed by a dentist. The material may be cheaper than the traditional splint, but there is still a specific labor cost of the dentist that must be done. And the patient must wait until the dentist carves a right shape for the patient. Also, because the anterior guidance that is created is flat therefore the vertical dimension of the entire appliance will be larger even when the patients' mandible is at rest, not necessarily just in an excursion. This increase in vertical dimension could be so excessive as to preclude many patients from being able to utilize NTI-tss.

U.S. Pat. No. 4,773,854 to Weber disclosed herein is a device for the representation of condylar movements of a patient and their correct simulation which includes models of sets of teeth to determine the required corrections to the biting surfaces in order to obtain ideal occlusion. The device includes an articulator with the lower part thereof able to be brought into a predetermined three-dimensional relation with respect to an upper part of the articulator and having two blocks having guide elements on the lower part of the articulator to support condyle balls of the upper part of the articulator. The device further includes a lower jaw recording bow and an upper jaw recording bow which can be brought into an active and predetermined relation with respect to the articulator and which disposes of at least three recording plates with corresponding recording pins as well as positioning spoons for the combination of a lower jaw dentition model. With this device, opening movements of articulation may be recorded three-dimensionally so that three clear crossing points are created for the occlusion.

U.S. Pat. No. 4,901,737 to Toone discloses an intra-oral appliance for reducing snoring which repositions the mandible in an inferior (open) and anterior (protrusive) position as compared to the normally closed position of the jaw. Once the dentist or physician determines the operative "snore reduction position" for a particular patient, an appropriate mold is taken of the maxillary dentition and of the mandibular dentition for formation of the appliance template. The Toone appliance includes a pair of V-shaped spacer members formed from dental acrylic, which extend between the maxillary and mandibular dentition to form a unitary mouthpiece. In an alternative embodiment of the Toone invention, the spacer members are formed in two pieces and a threaded rod is provided to enable adjustment of the degree of mandibular protrusion or retrusion after the mouthpiece is formed.

European patent application No. 0,312,368 published also discloses an intra-oral device for preventing snoring. This device consists of a U-shaped mouthpiece, which conforms to the upper dental arch of the user and includes a sloped, lower ramp for engaging the mandibular dentition. Normal mouth motions, such as the clenching of the jaw, will cause some of the mandibular dentition to engage the underside of the ramp, thereby camming the lower jaw forward to increase the spacing between the base of the tongue and the posterior wall of the pharynx.

U.S. Pat. No. 5,722,828 to Halstrom discloses an apparatus and method for producing a gothic arch tracing representative of the natural range of motion of a patient's mandible. The apparatus consists of a kit including a mandibular bite rim having a tracing plate; a maxillary bite rim having a tracing arm; and a stylus releasably connectable to the tracing arm for extending between the tracing arm and the tracing plate externally of the patient's mouth. The stylus has a marker on one end thereof for drawing a gothic arch tracing on a removable paper substrate, such as a post-it note, attachable to the tracing plate. The tracing is used in the fabrication of a dental bite registration mold for the patient. The mold may in turn be used to mount casts of the patient's dentition in a specific relationship as required for prosthetic or therapeutic purposes.

Frank et al, disclosed a full contact splint with anterior guidance on the internet at address http://www.greatlakesortho.com/content/files/resources/SplintApplianceSelectionGuide_S222.pdf. The full contact splint with anterior guidance is to form an anterior guidance under the lower surface of the maxillary retentive piece. However, developing anterior guidance directly to the lower surface of the maxillary retentive piece is very time consuming trial and error job and expensive for both of dentist and patient.

From the above prior arts it is found that none of the prior art provides the ability to treat bruxism, and TMD to include a broad range of malocclusions as economical, as easy to apply, and medically safe as the anterior guidance package (AGP) as provided in the current application.

SUMMARY OF THE INVENTION

Many people who inappropriately brux or clench also have the complicating factors of a mal-occlusion that cause discrepancy between centric occlusion and centric relation. Another factor that can amplify the pain and damage potential of bruxing/clenching is inadequate anterior guidance. Bruxism and bruxism combined with these factors can cause myofacial pain syndrome and many other types of damage to the teeth, muscles, TMJ (Temporo-mandibular Joint) and other tissues. Many kinds of 'Night Guards' have been provided to allow the mandibular condyles to locate in their most comfortable position by freeing the mandible from malocclusions and posterior interferences. Anterior guidance is a physical limitation of all excursions of the jaw. Elimination of centric relation/centric occlusion discrepancies allows the patient to be free of their malocclusion to allow the patients' jaw to acquire centric relation position. Anterior guidance and freedom of the jaw from centric relation/centric occlusion discrepancies can be provided in a custom fabricated and custom adjusted acrylic night guard made by a dentist on the occlusal/incisal surface of the maxillary teeth or mandibular teeth. However, a dentist must spend a great deal of time and effort to create and modify a customized night guard for the patient to create anterior guidance and relief from centric occlusion/centric relation discrepancy in consideration of their particular malocclusion. It also burdens the patient with time and cost. It is the purpose of the current invention to provide an anterior guidance package for a splint, superior anterior guidance installed night guard, which is more affordable for patients and easier to create for dentists, even for a non-dentist. Another purpose of the current invention is to provide an anterior guidance package for an easy to make anterior guidance installed night guard for patients of various malocclusions. Another purpose of the current invention is to provide three dimensional control and limits to the front end of the mandible to provide treatments for other maladies to include meniscus displacement, clinical closed lock of the TMJ, and various other disorders of the jaw, teeth, muscles and other tissues of mastication and mouth. A pre-fabricated, pre-programmed or custom-made guidance assembly Anterior Guidance Package (AGP) is provided. The anterior guidance package of current invention is comprised of one maxillary guidance component and one mandibular guidance component. Those guidance components are attached to a maxillary retention piece and a mandibular retention piece of a splint, respectively, to provide superior anterior guidance to the mandible. An AGP splint kit according to current application can provide a fast, inexpensive, easy way to construct a high quality anterior guidance equipped night guard (orthotic appliance) that will be superior to a custom appliance constructed by a dentist. The AGP of current invention is produced in many different shapes and sizes and can be indexed in centric relation or some other position based on the patients' diagnosis, and therapy or treatment being provided to the patient.

BRIEF DESCRIPTION OF DRAWINGS

FIG. 16-a is a perspective cross-sectional view of the mandible hinging up in centric relation indexing a bruxism AGP for a patient with or without a complex malocclusion onto the special retentive pieces when the mandible is in centric relation and the vertical dimension is appropriate according to the first contact.

FIG. 16-b is perspective view of the special retention piece and the height adjustable shelf for a bruxism AGP for a patient with or without a complex malocclusion.

DETAILED DESCRIPTION OF THE PREFERRED EMBODIMENT

A splint called a 'night guard' is a hard material built on either maxillary and/or mandibular teeth. It is custom fabricated and custom adjusted by a dentist to provide anterior guidance and eliminate posterior interferences. The splint allows the patient to be free of their malocclusion and allows the patient to acquire centric relation position. Usually a dentist customizes a splint for a particular patients' malocclusion, typically an acrylic splint on one arch opposing natural teeth.

These are expensive appliances because a dentist must spend the time custom creating and custom modifying the night guard to provide anterior guidance and eliminate posterior interferences for the patient in consideration of their particular malocclusion. The patient does still inappropriately clench/brux, albeit with much less force, overall pain and damage. So, the applicant developed an Anterior Guidance Package (AGP) that makes a night guard easier to construct, more affordable for a patient and saves dentist's time.

Figure 1:
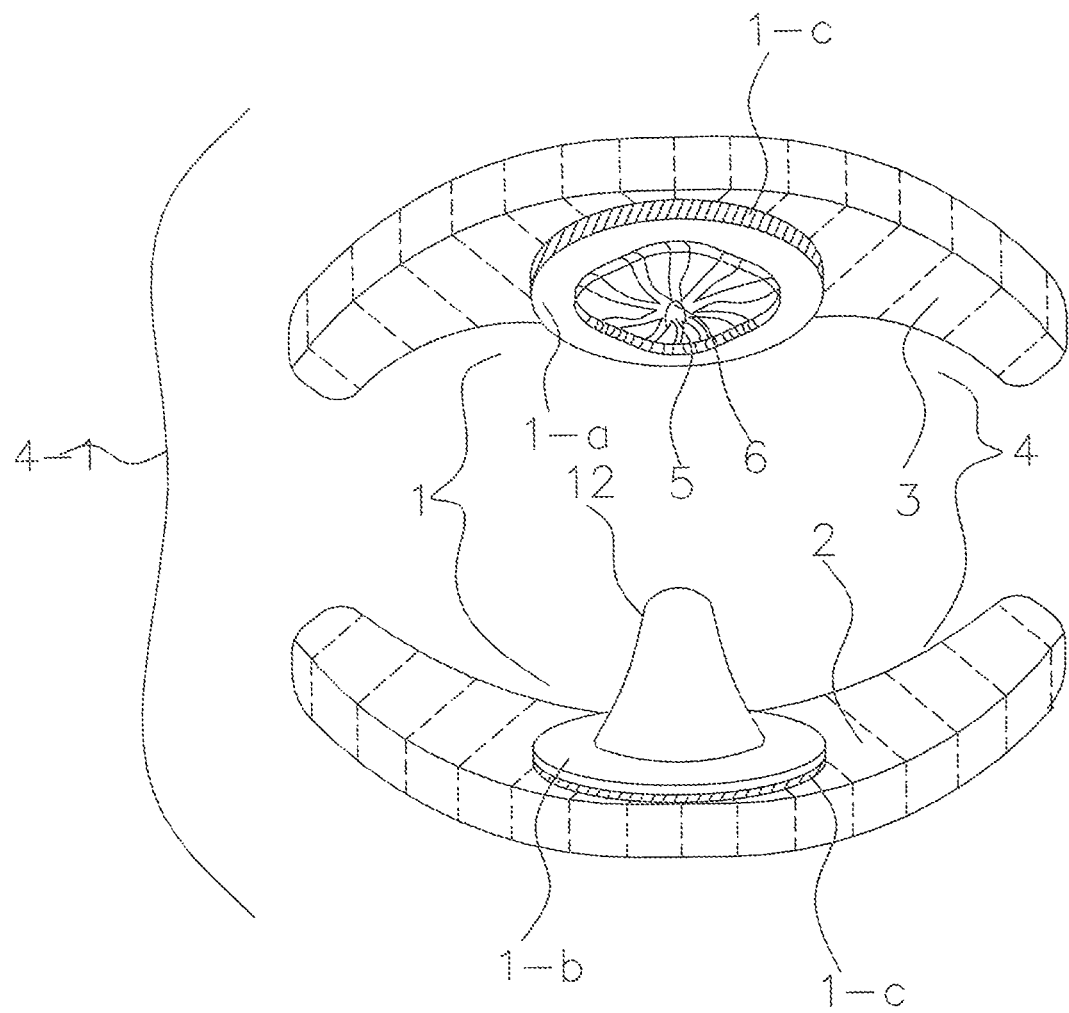
FIG. 1 is an exploded view of the Anterior Guidance Package (AGP) according to current invention connected to a mandibular retention piece and a maxillary retention piece of a splint.

FIG. 1 is an exploded view of the Anterior Guidance Package (AGP) (1), according to current invention connected to a mandibular retention piece (2) and a maxillary retention piece (3) of a splint (4) by adhesive filler (1-c).

The Anterior Guidance Package (1) of current invention is a pre-fabricated, pre-programmed or custom-made guidance assembly. The Anterior Guidance Package (1) of current invention is comprised of one maxillary guidance component (1-a) and one mandibular guidance component (1-b). Those guidance components (1-a), (1-b) are attached to the maxillary retention piece (3) and the mandibular retention piece (2) of a splint (4), respectively, by proper means of attachment to provide superior anterior guidance to the mandible. The proper means of attachment includes, but not limited to adhesive filler glue, screws and pins, etc. These designs can be standardized or individualized based on many variables and goals but generally will provide to a patient ideal anterior guidance and the elimination of centric occlusion/centric relation discrepancies. The anterior guidance package (AGP) (1) could be any of many designs. In contrast to a splint that is customized against the dentition of the opposing dental arch or even one splint opposing another splint, the components of the Anterior Guidance Package AGP (1) according to current invention can provide a wide range of features for broad application including the replication of ideal anterior guidance of teeth as would be found in an ideal occlusion. The AGP (1) according to current invention can be of any three dimensional patterning, steepness of inclination and many other design considerations dependent upon the purpose.

1. Traditional Procedure of Providing Anterior Guidance to a Patient

In order to apply an anterior guidance equipped splint to a patient in a traditional procedure the dentist would:
Create an acrylic splint on the teeth of either the maxillary or the mandibular arch.
Using articulation paper to mark the contacts of the opposing teeth or an opposing splint in centric relation on the acrylic splint, the dentist will carve the acrylic developing both anterior guidance and the elimination of posterior interferences in the acrylic splint. He will polish the night guard and deliver it to the patient. This procedure must be done by a dentist who has broad knowledge of how the gnathostomatic system works. These night guards are therefore time consuming and expensive for the patient because every time the dentist creates a night guard he develops by gradual and time consuming carving the anterior guidance and the elimination of interferences in centric relation until it fits the patient.

2. Procedure of Applying Pre-Programmed AGP of Current Invention to a Patient.

From the long period of practicing as a dentist, the inventor found that most average adults have anterior guidance that if it were ideal, fit within specific relative dimensions and patterning.

Figure 2:
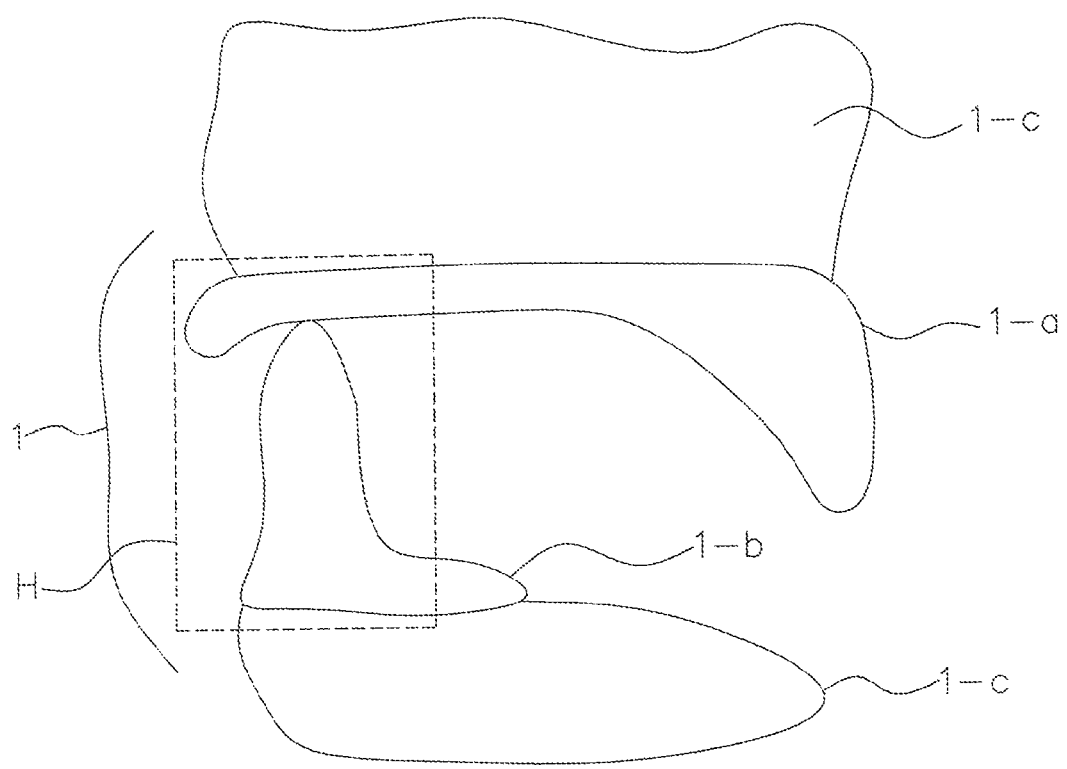
FIG. 2 is a cross-sectional side view of the Anterior Guidance Package (AGP) assembled in its correct orientation by a removable holder before it is indexed onto the maxillary and mandibular retentive pieces.

FIG. 2 shows a cross-sectional view of the not as yet separated AGP of current invention before it is indexed onto their respective retentive pieces. The holder (H) keeps the AGP (1) package together in its correct orientation until the components of the AGP are indexed appropriately in centric relation and in vertical dimension.

Figure 3:
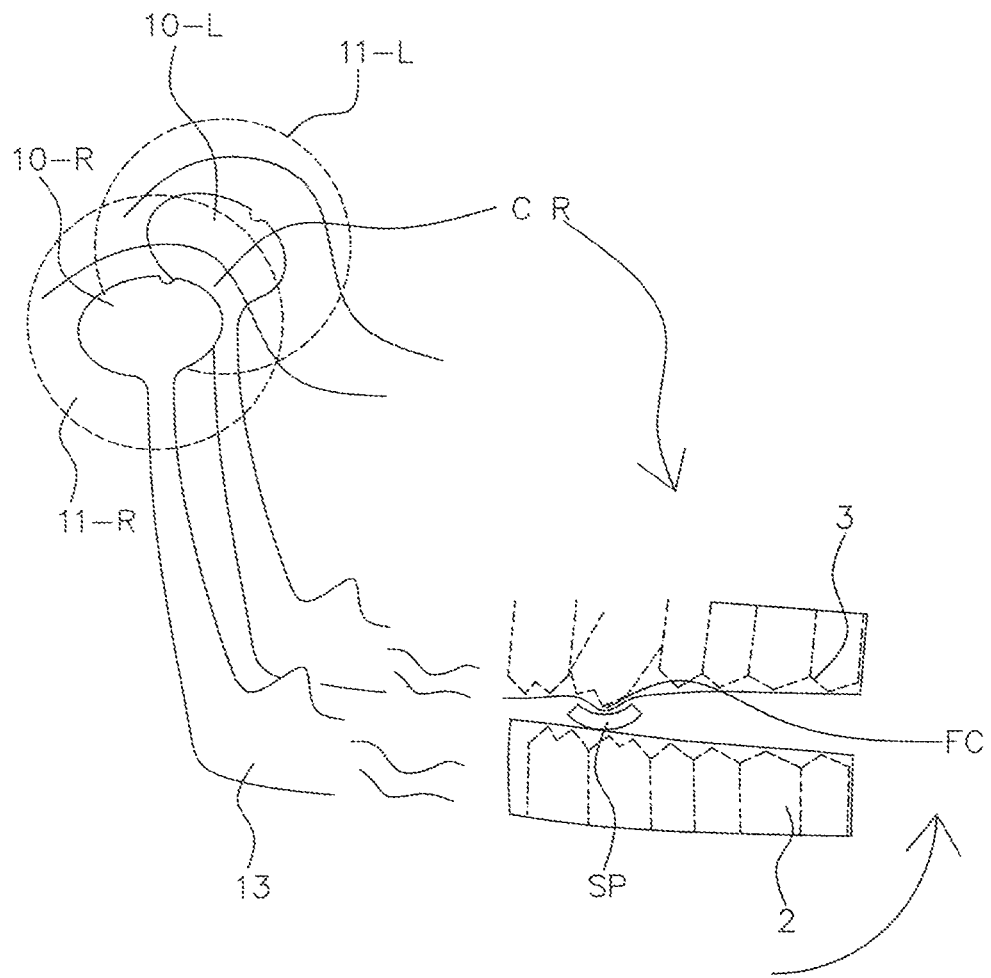
FIG. 3 is a perspective cross-sectional view of the mandible hinging up in centric relation finding the first contact on teeth or retentive pieces and placing a spacer at that location.

FIG. 3 shows the maxillary arch with the maxillary retentive piece (3) molded onto the maxillary teeth and the mandibular arch with a mandibular retentive piece (2) molded onto mandibular teeth hinging up in centric relation (CR).

First the operator (usually a dentist) identifies what is the first contact (FC) in centric relation (CR). When the mandible (13) is hinged up in centric relation, the position of the first contact (FC) of teeth or retentive pieces is variable dependent upon the malocclusion of that particular patient and is most often an inappropriate posterior contact.

A 1 mm sticky but removable spacer (SP) is placed on that first contact.

Next the mandible (13) is hinged again up in centric relation and the AGP (1) of current invention is indexed in the most anterior area of both the maxillary (3) and mandibular (2) retentive pieces respectively.

Figure 4:
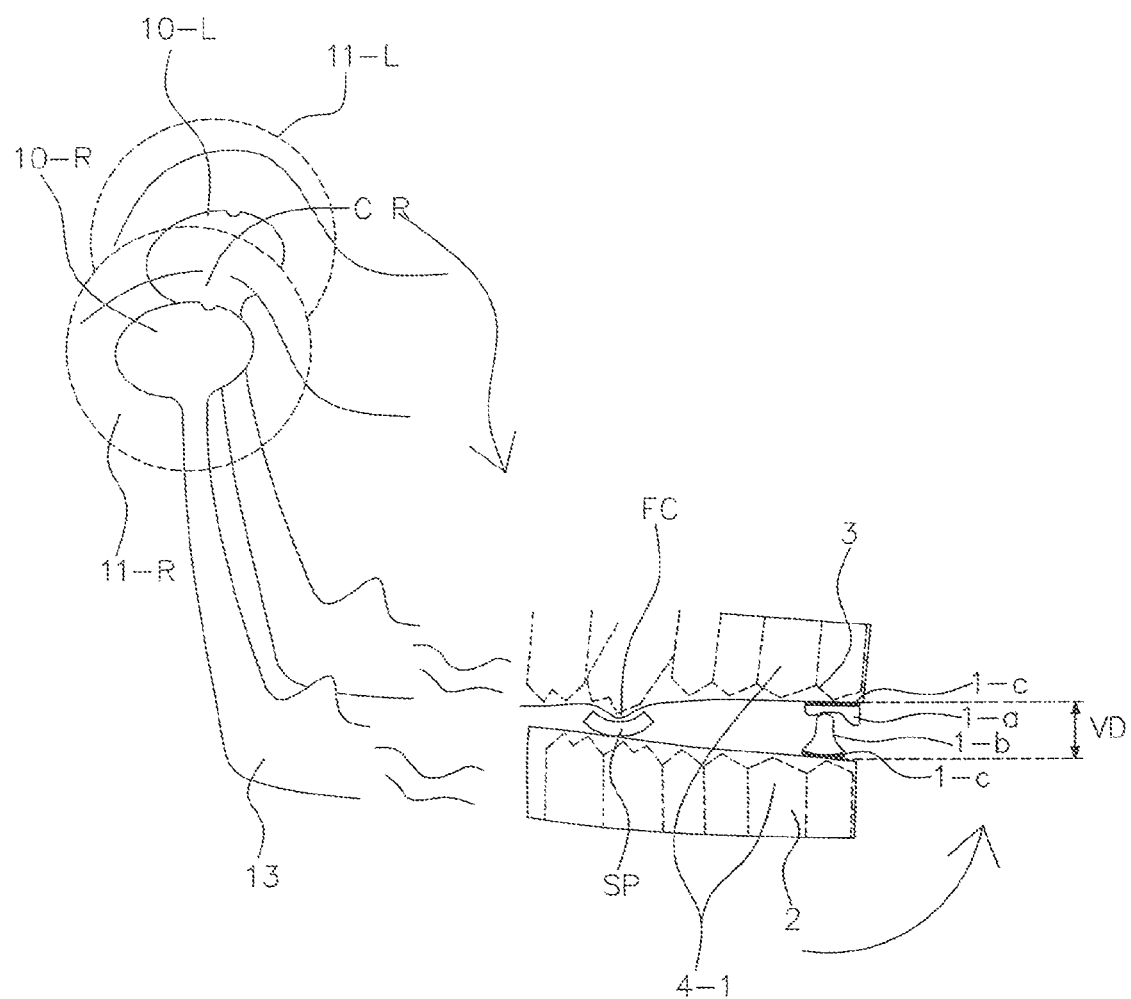
FIG. 4 is a perspective cross-sectional view of the mandible hinging up in centric relation indexing the Anterior Guidance Package (AGP) onto the retentive pieces when the mandible is in centric relation and the vertical dimension is appropriate according to the first contact.

FIG. 4 shows the AGP (1) of current invention placed on the anterior inferior surface of the maxillary retentive piece using adhesive filler (1-c). Adhesive filler (1-c) is already placed on the surface of the AGP (1) as shown in FIG. 2. As the jaw is hinged up in centric relation and the sticky but removable spacer (SP) touches the opposing arch at first contact (FC), the adhesive filler (1-c) is displaced from the superior and inferior surface of the AGP (1) of current invention to define the vertical dimension (VD) for a splint (4-1) that is equipped with the AGP (1) of current invention for that particular patient. Also, the maxillary guidance component (1-a) is indexed onto the maxillary retentive piece (3) and the mandibular guidance component (1-b) is indexed onto the mandibular retentive piece (2) according to the centric relation (CR) position of the mandible (13).

The adhesive filler (1-c) left between the retention pieces (2), (3) and guidance components (1-a), (1-b) is hardened and both components (1-a), (1-b) of the AGP (1) of current invention become rigidly affixed to their respective retentive pieces (2), (3). Then remove the holder (H) from the AGP (1) and the mandibular guidance component (1-b) is separated from the maxillary guidance component (1-a).

The sticky but removable 1 mm spacer (SP) is removed.

The effect is that the AGP (1) of current invention is now indexed appropriately for whatever occlusion or malocclusion a patient may have to provide ideal anterior guidance and in the appropriate vertical dimension to eliminate all centric occlusion/centric relation discrepancies (or posterior interferences) after the spacer (SP) is removed in the centric relation position of that particular patient.

Figure 5:
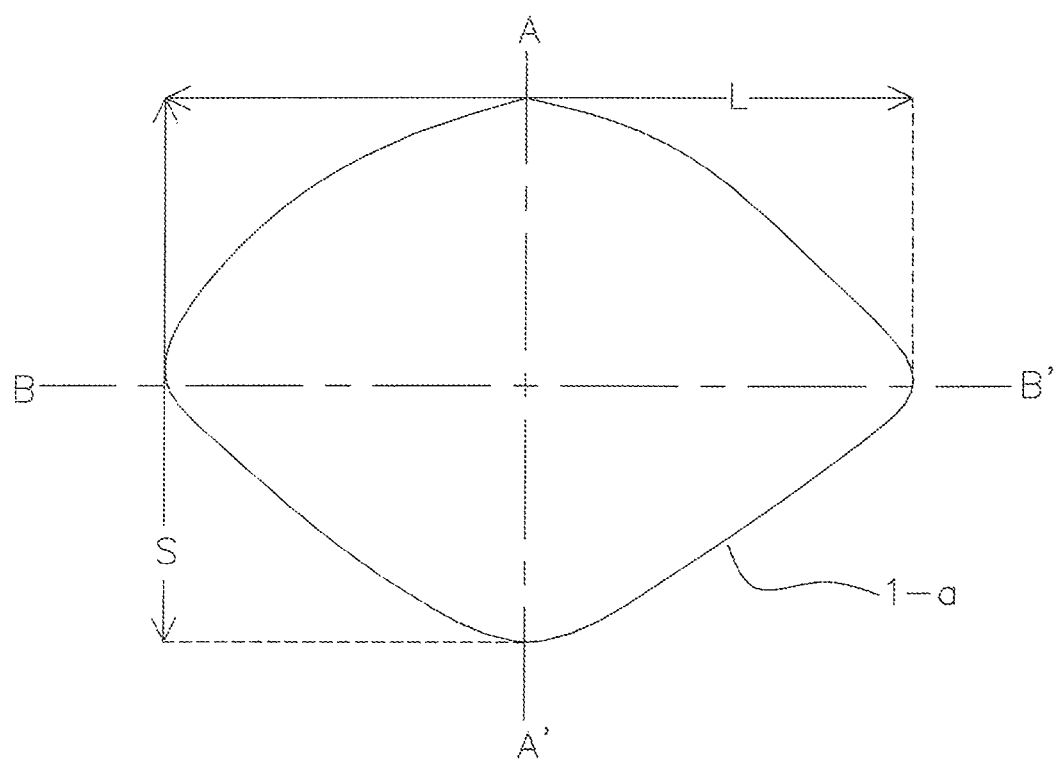
FIG. 5 is a plane view of the maxillary guidance component of the AGP of current invention.

FIG. 5 is a plane view of the maxillary guidance component (1-a) of the AGP (1) of the current invention. The plane view of the maxillary guidance component (1-a) is a square-ovoid shape. The overall shape of the maxillary component (1-a) of the AGP (1) is including, but not limited to, a smoothly rounded square, smoothly rounded oval, smoothly rounded pentagonal, smoothly rounded hexagonal shape. According to dental literature and the inventors experience, it was found that the long axis (L) of the square-ovoid shape maxillary guidance component (1-a) of the AGP (1) is less than 35 mm, preferably less than 25 mm and the short axis (S) of the square-ovoid shape maxillary guidance component (1-a) is less than 20 mm, preferably 12 mm. However, the shape and dimension of the maxillary guidance component (1-a) of the AGP (1) of the current invention is varied depending on the patients' size, dentition, TMJ situation, diagnosis, intent to index in centric relation or some other position, treatment, and the nature of the guidance and limits intended by the operator.

Figure 6:
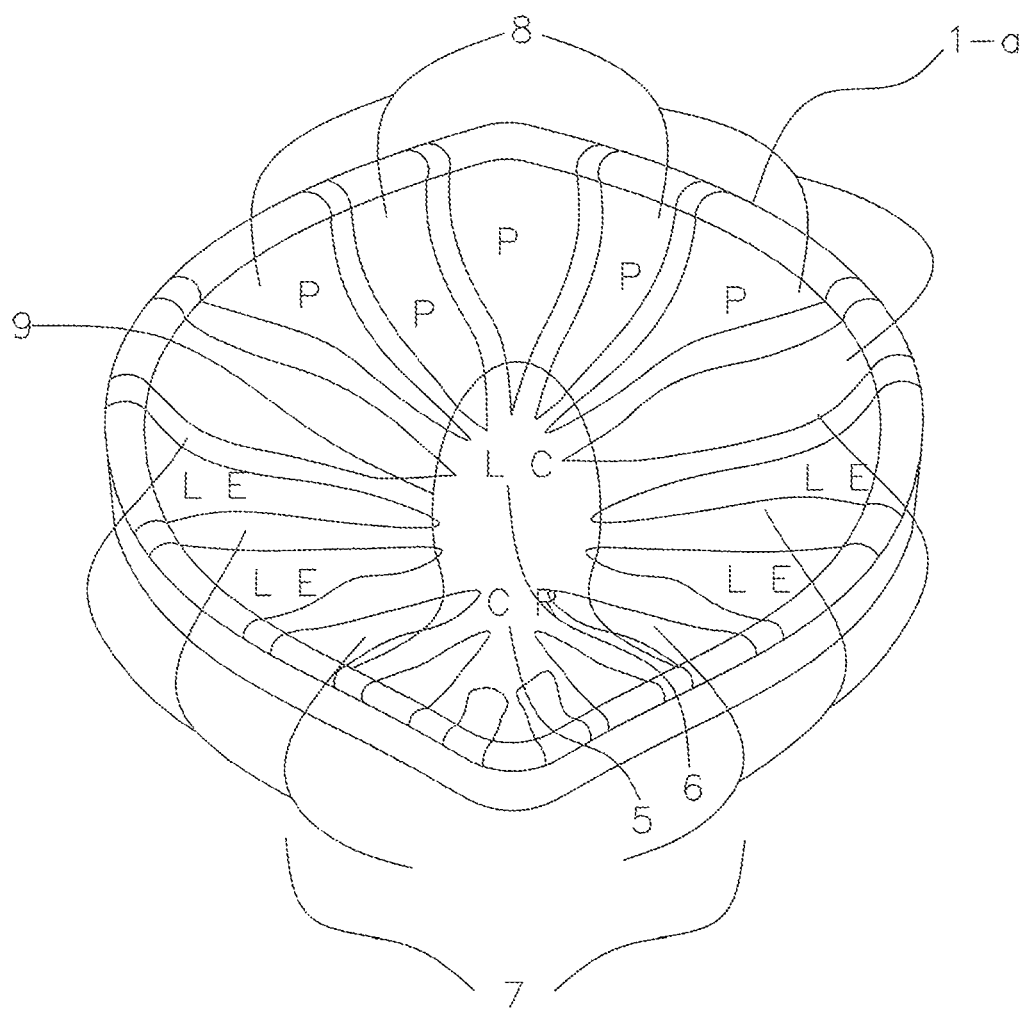
FIG. 6 is a view of the internal topography of the maxillary guidance component of the AGP showing the specific guidance of a centric relation stop, long centric area, lateral excursion guidance, and protrusive guidance.

As shown in FIG. 6, the perspective view of the maxillary guidance component (1-a) of the AGP (1) has a flat area for a stable centric relation stop (CR) (5) extended into a further area of flat for the long centric position (LC) (6) of the mandible extending laterally and anteriorly into blended inclines of a concave shape for lateral excursion guidance (LE) (7) and protrusive excursion guidance (P) (8) to provide ideal anterior guidance to the patient's mandible by the mandibular guidance component (1-b) against these features of the maxillary guidance component (1-a) to minimize muscular force and avoid all posterior interferences. This feature of appropriate anterior guidance which discludes the mandible downward (inferiorly) in its excursions allows for a night guard of significantly less vertical dimension (VD) when the patient is at rest than other designs, much like an ideal occlusion would.

Figure 7:
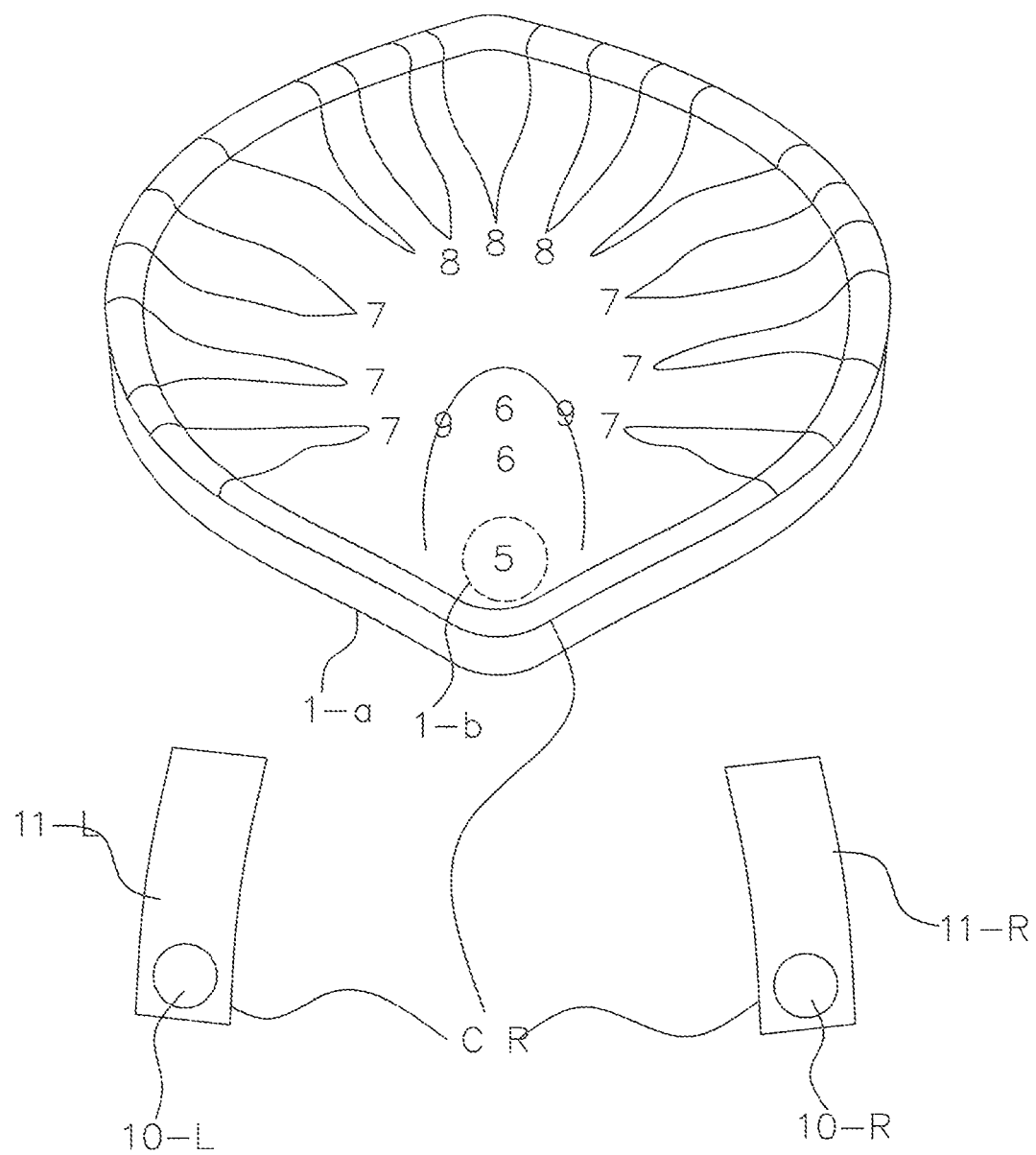
FIG. 7 is a superior transparent view of the AGP of current invention correlating the centric relation position of the TMJs coincident with the indexing of the AGP, and the available guidance to the mandibular guidance component from the maxillary guidance component from the position of centric relation.

FIG. 7 shows a superior transparent view of the AGP (1) of current invention. It shows how the AGP (1) of current invention replicates ideal anterior guidance as defined in current dental literature and the experience of the inventor. In FIG. 7 point (5) represents where the mandibular guidance component (1-b) sits at rest in the maxillary guidance component (1-a) when the condyle (10) of the temporomandibular joint (TMJ) (11) of the mandible is in its centric relation (CR) position. As a patient functions or bruxes his mandible, the mandibular guidance component (1-b) provides ideal anterior guidance for the mandible by means of the mandibular guidance component (1-b) functioning against the maxillary guidance component (1-a) in the position of centric relation (5), long centric (6), lateral excursions (7), and protrusive guidance (8). The AGP (1) of current invention provides ideal anterior guidance without regard to the position of teeth, the condition of teeth or missing teeth.

To apply the pre-programmed AGP (1) of the current invention to a patient the following items are needed;
1) One pre-fabricated AGP (FIG. 2 is a cross-sectional side view of the pre-fabricated AGP kit (1) before it is indexed to a patient's retentive pieces). The pre-fabricated AGP (1) kit is assembled and held by a holder (H),
2) one mandible retention piece (2), (The mandibular retention piece could be full arch or less coverage but must be highly retentive and stiff. It would be easily moldable to the patients' lower teeth and very thin.),
3) one maxillary retention piece (3) (moldable, highly retentive, stiff and thin),
4) one 1 mm sticky but removable spacer (SP),
5) adhesive filler (1-c), and
6) dryer or light curing unit should be prepared.

When those items are ready;
(A) Apply to the patient the maxillary retention piece (3) and mandibular retention piece (2) on his/her teeth.
(B) Place the patient's mandible into centric relation position and identify the first contact (FC) (A point that touches first when the mandible is hinged up in centric relation. This point is highly variable from person to person dependent upon their malocclusion. It will be in the posterior segment for most people.)
(C) Then place a sticky 1 mm but removable spacer (SP) on that first contact (FC).
(D) Place the AGP (1) in the anterior inferior aspect of the maxillary retentive piece (3). The outer surface (superior and inferior) of the anterior guidance components (1-a), (1-b) is covered with adhesive filler (1-c).
(E) Hinge the mandible in centric relation up toward the maxilla and when the 1 mm sticky spacer touches (SP) the first contact (FC), index the mandibular guidance component (1-b) onto the mandibular retentive piece (2). Both components (1-a), (1-b) of the AGP (1) have now been indexed appropriately to each respective retentive piece (2),(3) in the correct vertical dimension (VD) by displacing the adhesive filler (1-c) to that vertical dimension. Also both components (1-a), (1-b) have been indexed appropriately anteriorly-posteriorly for that particular patients centric relation (CR) position. Both components (1-a), (1-b) of the AGP (1) should now be adhered rigidly with the 1 mm thick sticky spacer (SP) still on the first contact point.
(F) Dry or polymerize the adhesive filler (1-c) with a dryer or a light cure unit to compensate for the gap between the retention pieces (2), (3) and the anterior guidance components (1-a), (1-b) and adhere solidly and rigidly.
(G) Take the entire assembly (4-1) out of the patients' mouth. Then remove the 1 mm sticky spacer (SP) from the first contact (FC), and remove the holder (H) from the AGP (1).

The AGP (1) equipped night guard (4-1) is now ready for use.

The above described procedure provides a superior night guard to any previous method, and is much simpler to construct than any traditional or previous method of creating a night guard.

In the traditional method, carving anterior guidance and eliminating posterior interferences on an acrylic platform can take multiple appointments, and takes significant time of a dentist who has extensive knowledge of the gnathostomatic system.

But, in the new method utilizing the AGP (1), the entire process can happen in one appointment in significantly less time and could be accomplished by an individual with significantly less training.

Figure 8:
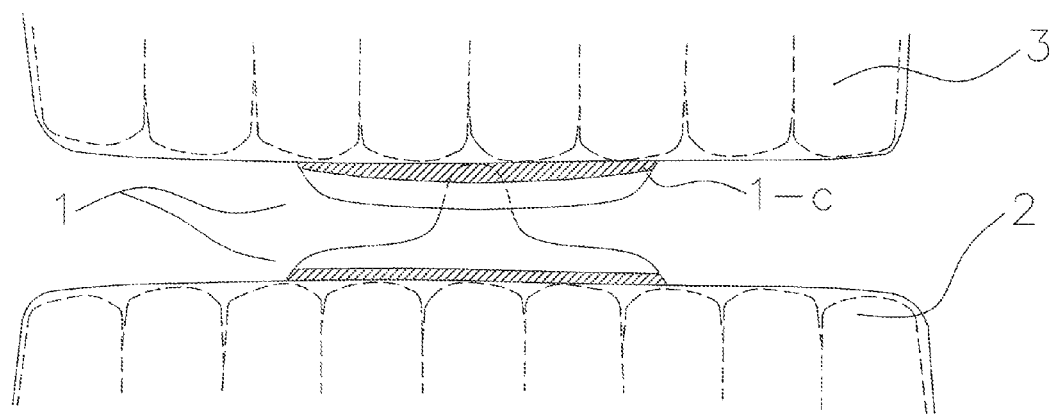
FIG. 8 is a frontal view of AGP of current invention solidly adhered on retentive pieces by adhering filler and worn by a patient.

FIG. 8 is a frontal view of the AGP (1) of the current invention solidly adhered on retention pieces (2), (3) by adhering filler (1-c) and worn by a patient.

Since the role of anterior guidance is to limit and guide the movement of the mandible while a patient is wearing the AGP splint (4-1), a threshold (9) of continuous lateral and protrusive guidance is developed along the face of the maxillary guidance component (1-a).

Figure 9:
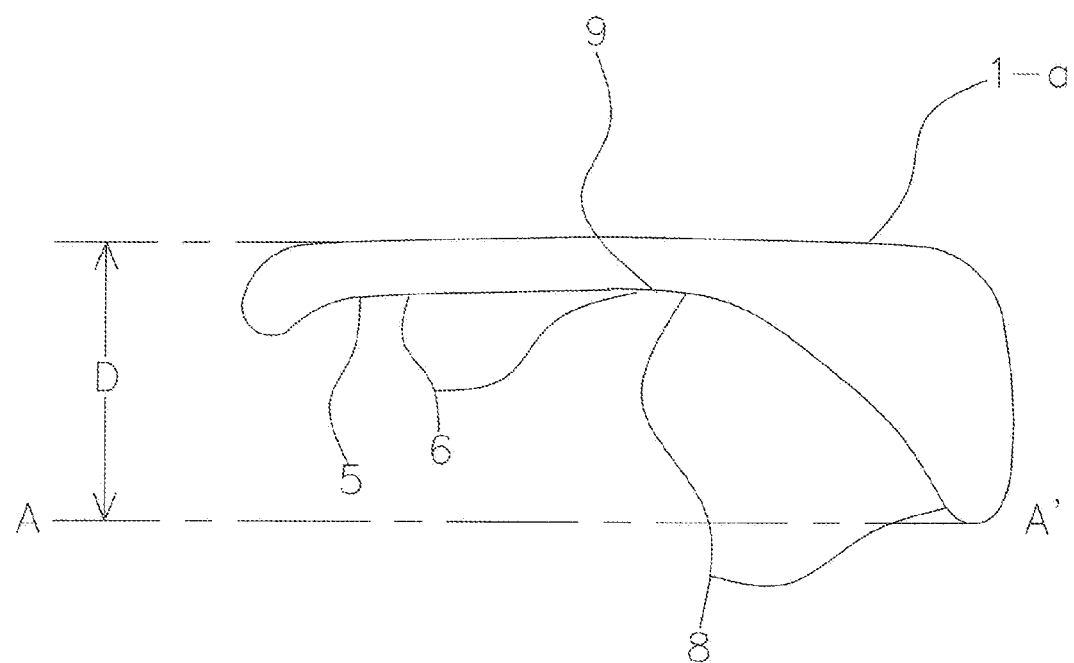
FIG. 9 is an enlarged cross sectional view of the maxillary guidance component of the AGP according to current invention along the line A-A'.
Figure 10:
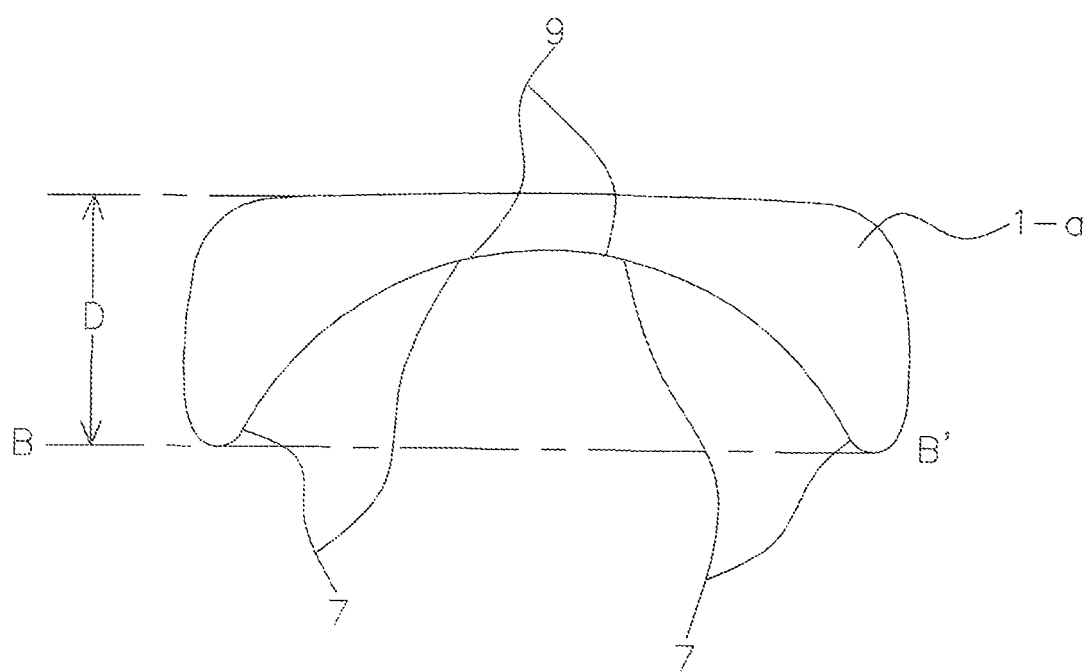
FIG. 10 is an enlarged, cross sectional view of the maxillary guidance component of the AGP according to current invention along the line B-B'.

FIG. 9 and FIG. 10 are enlarged cross sectional views of the maxillary guidance component (1-a) of the AGP (1) according to current invention along the lines A-A' and B-B' in the FIG. 5. The threshold (9) is smoothly extended to the concave internal surface of the maxillary guidance component (1-a). However, this concave internal surface may be altered to an asymmetrical concave surface based on the malocclusion or other special considerations of a particular patient. The internal concave shape can also be of different shapes dependent upon the type of guidance the operator proscribes and the shape of the mandibular guidance component that will be used (see FIGS. 16-20). The depth (D) of the maxillary guidance component (1-a) is, including but not limited to, 1 to 5 mm, preferably 4 mm.

Figure 11:
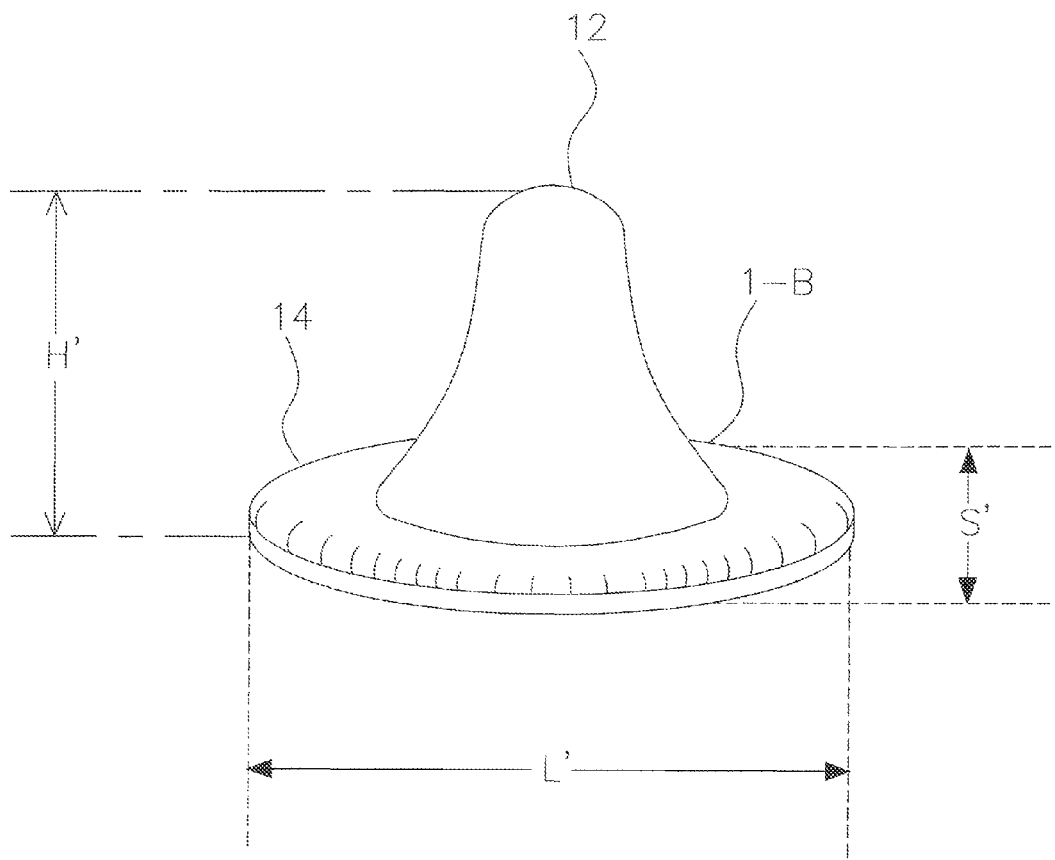
FIG. 11 is a perspective view of the mandibular guidance component of the AGP of current invention.

FIG. 11 is a perspective view of mandibular guidance component (1-b) of the AGP (1) according to current invention. The base (14) of the mandibular guidance component (1-b) has the square ovoid shape and same dimension as the maxillary guidance component (1-a) as shown in the FIG. 4.

The length of the long axis (L') of the oval shaped mandibular guidance component (1-b) is, including but not limited to, between 15 to 35 mm. And the length of the short axis (S') of the oval shaped mandibular guidance component (1-b) is, including but not limited to, between 8 to 20 mm.

A smooth rounded protrusion (12) is developed on one surface of the square ovoid shaped mandibular guidance component (1-b). Tip of the protrusion (12) is engaged in the flat to concave inner surface of the maxillary guidance component (1-a) and guides and limits the movement of a patients' mandible. Height of the smooth protrusion is, including but not limited to, between 1 to 6 mm, preferably 5 mm. However, the shape, size and dimension of the mandibular guidance component (1-b) of the AGP (1) of the current invention is varied depending on the patients' size, dentition, TMJ situation, diagnosis, treatment, intent to index in centric relation or some other position, and the nature of the guidance and limits intended by the operator (see FIGS. 16-20).

Figure 12:
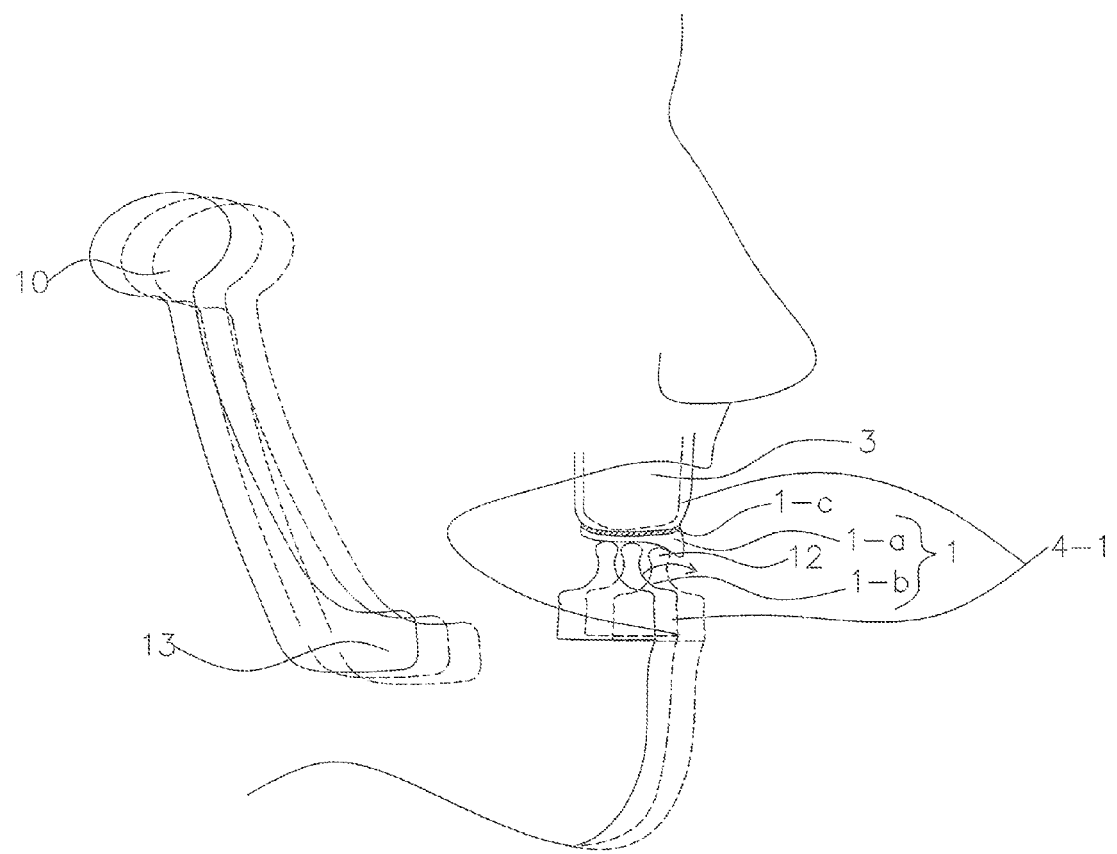
FIG. 12 is an enlarged, cross-sectional side view of movement of the mandible of a patient wearing the AGP equipped night guard.

FIG. 12 is an enlarged, cross-sectional side view of protrusive movement of the mandible (13) of a patient wearing the AGP (1) equipped night guard (4-1). When a patient, who has a habit of bruxism/clenching, is wearing AGP (1) equipped night guard (4-1) of the current invention, the patients mandible will experience appropriate protrusive guidance, guiding the jaw inferiorly.

Figure 13:
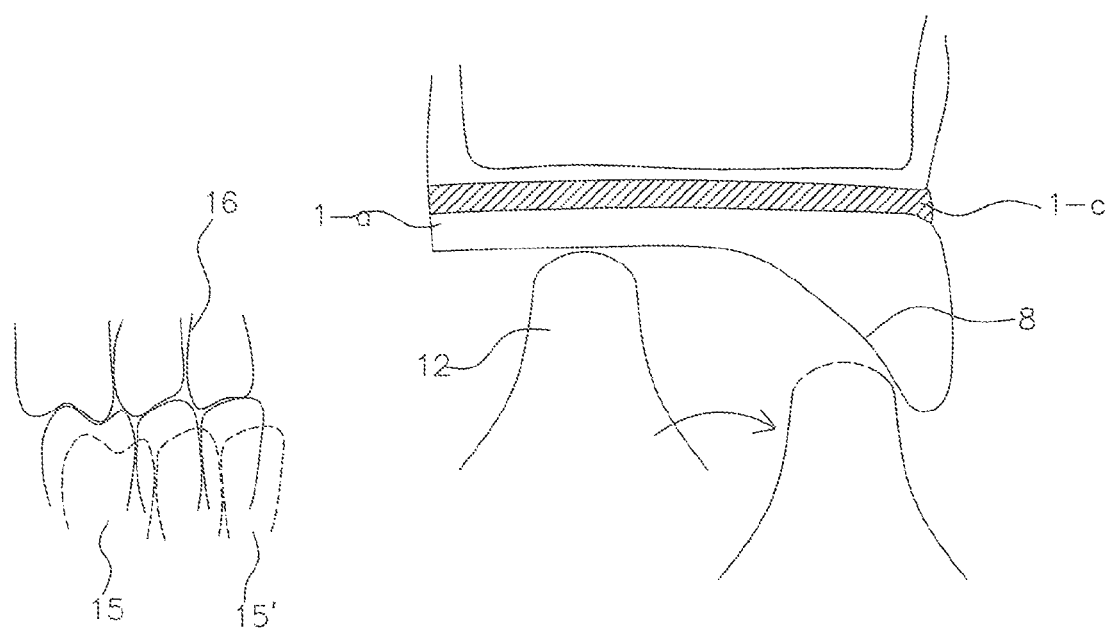
FIG. 13 is a more enlarged schematic drawing that shows how the appropriate protrusive guidance provided by the AGP of the current application eliminates posterior interferences when a patient is bruxing protrusively.

FIG. 13 is a more enlarged schematic drawing that shows how the appropriate protrusive guidance (8) provided by the AGP (1) attached to the night guard (4-1) to eliminate posterior interferences when a patient is bruxing protrusively. When a patient closes his mandible to function or brux, whether in an appropriate occlusion or a malocclusion, the intercuspation of the teeth as they mesh will bring maxillary tooth cusp inclines (16) and mandibular tooth cusp inclines (15) into close proximity or touching (whether they have the thin retentive material on them or not). In a protrusive excursion of the mandible, without the appropriate anterior protrusive guidance of the AGP (1) of current application, these inclines (15), (16) would collide potentially damaging the teeth, but also these deviating inclines (posterior interferences) would give a proprioceptive message to the muscles to deviate over these posterior interferences, therefore stimulating the muscles to hold the mandible in this deviated position ultimately placing the TMJ into an inappropriate position and leading to muscle spasticity or possible TMJ or other damage. If the guidance were flat like some previous systems, the vertical dimension of the entire appliance must be increased dramatically to avoid these interferences. Therefore even when the mandible is at rest in centric relation, and not even in an excursion, the vertical dimension of the entire appliance would be so excessive, that for many patients, it could not be used or at a minimum be more uncomfortable as compared to the AGP splint (4-1). The AGP (1) of current application solves the vertical dimension problem because it gives appropriate protrusive anterior guidance (8) also in a vertical way using the smooth protrusion (12) of the mandibular guidance component (1-b) guiding the mandible downward (inferiorly) therefore avoiding collisions of these tooth inclines (15), (16) or the production of unwanted and inappropriate muscle engrams, much like ideal tooth anterior guidance gives to an ideal occlusion.

Figure 14:
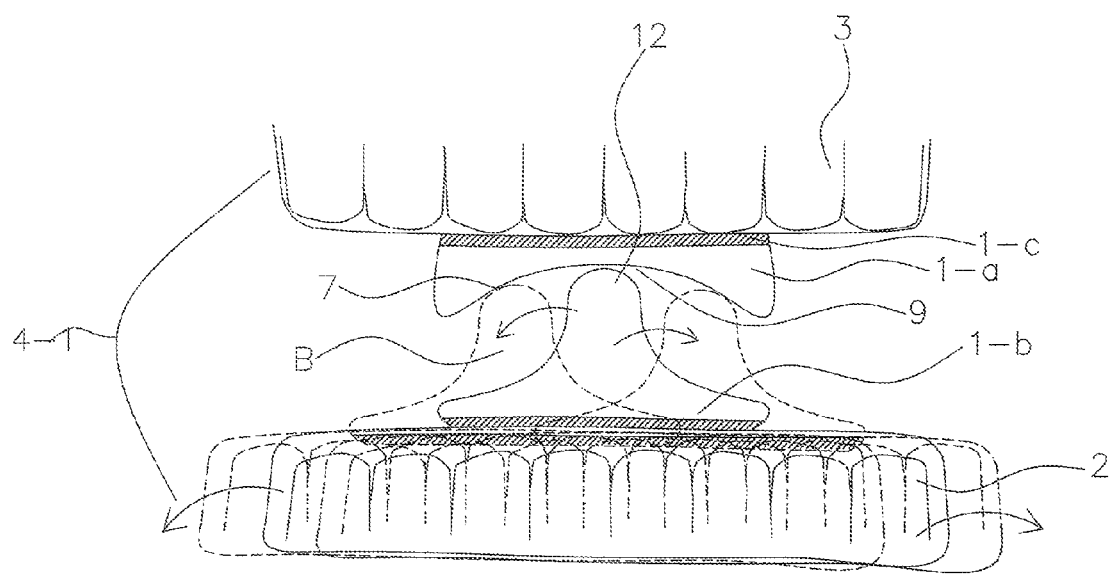
FIG. 14 is an enlarged, cross-sectional front view of movement of the mandible of a patient wearing the AGP equipped night guard

FIG. 14 is an enlarged, cross-sectional front view of movement of the mandible/jaw of a patient wearing the AGP (1) equipped night guard (4-1). When a patient is experiencing bruxism/clenching and wearing the AGP (1) equipped night guard (4-1), his/her jaw/mandible (13) moves laterally left and right and receives appropriate lateral guidance, guiding the jaw downward (inferiorly).

Figure 15:
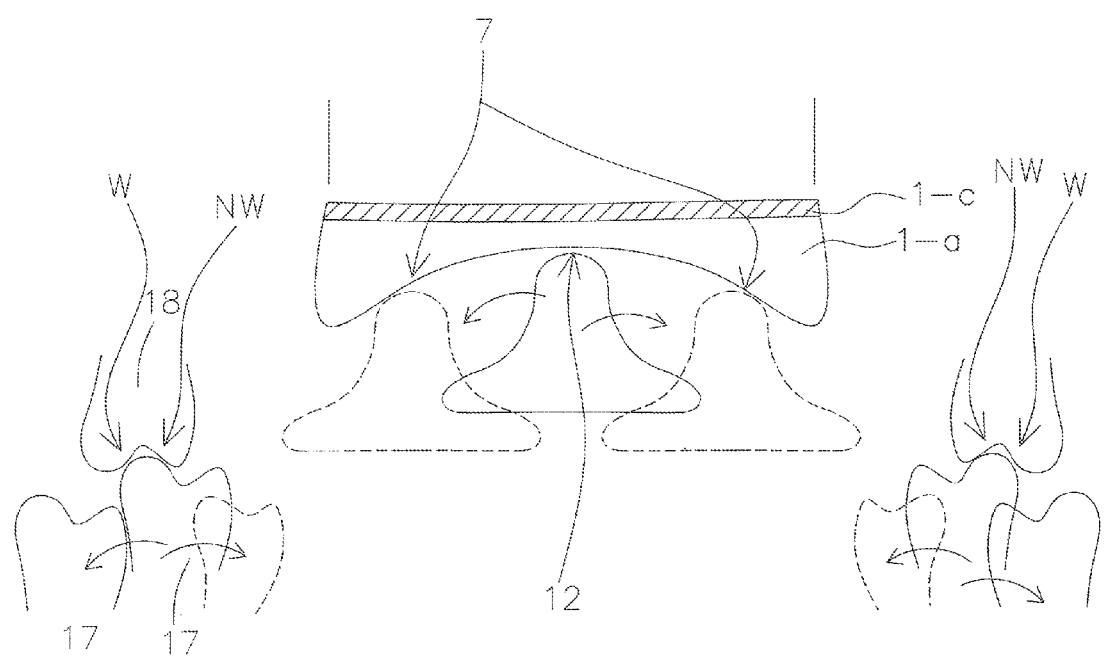
FIG. 15 is a more enlarged schematic drawing that shows the appropriate lateral guidance provided by the AGP of the current application that eliminates posterior interferences when the patient is bruxing in a left or right lateral excursion.

FIG. 15 shows the appropriate lateral guidance (7) provided by the AGP (1) attached to the night guard (4-1) to eliminate posterior interferences when the patient is bruxing in a left or right lateral excursion. When a patient closes his mandible to function or brux, whether in an appropriate occlusion or a malocclusion, the intercuspation of the teeth as they mesh will bring maxillary tooth cusp inclines (18) and mandibular tooth cusp inclines (17) into close proximity or touching (whether they have the thin retentive material on them or not). In a lateral excursion of the mandible, without the appropriate anterior lateral excursion guidance of the AGP (1) of current application, these inclines (17), (18) would collide potentially damaging the teeth, but also these deviating inclines (17), (18) (posterior interferences) could produce both working (W) and non-working (NW) interferences and would give a proprioceptive message to the muscles to deviate over these posterior interferences, therefore stimulating the muscles to hold the mandible in this deviated position, ultimately placing the TMJ into an inappropriate position, leading to muscle spasticity and possible TMJ or other damage.

If the guidance were flat like some previous systems, the vertical dimension of the entire appliance must be increased dramatically to avoid these interferences. Therefore even when the mandible is at rest in centric relation, and not even in an excursion, the vertical dimension of the entire appliance would be so excessive, that for many patients, it could not be used, or at a minimum would be more uncomfortable as compared to the AGP splint (4-1). The AGP (1) of current application solves the vertical dimension problem because it gives appropriate lateral excursion anterior guidance (7) also in a vertical way by guiding the smooth protrusion (12) of the mandibular guidance component (1-b) downward (inferiorly) much like ideal tooth anterior guidance gives to an ideal occlusion.

The most common use of the AGP (1) will be for the treatment and amelioration of bruxism, however the AGP (1) has the unique ability to control and limit the front end of the mandible three-dimensionally independent of malocclusion or condition of the patients' teeth. This revolutionary property offers a wide range of solutions for other maladies of the mouth, jaws and TMJ. When using the AGP (1), not only does the operator have three-dimensional control of the anterior of the mandible, but dependent upon the malady and treatment proscribed, the AGP (1) can be indexed in a position of the operators choosing other than centric relation to greatly expand the scope of treatments available.

Human malocclusions can be complex. In general they can be classified Class 1, 2 and 3. These occlusions/malocclusions can be further complicated by anterior and posterior crossbites, overjet, deep bite, open bite and other modifiers and combinations thereof. And unfortunately human occlusions and mal-occlusions are so diverse to each individual that a particular AGP cannot be assigned to a particular occlusion or malocclusion. In regard to bruxism splints, the goal in all these plethora of different occlusions and malocclusions in the context of bruxism, is to provide anterior guidance to neutralize posterior interferences to allow the mandible to function in the best stress bearing position of centric relation even under the stress of bruxism and to decrease muscle activity and spasticity giving protection to the teeth and the TMJ, reduction of myo-facial pain syndrome and migraine headache. By using one of the three choices of bruxism AGPs (FIGS. 2,16 and 17) in the construction of an AGP bruxism splint would provide a superior bruxism appliance to 95% of bruxism patients regardless their malocclusion.

Figure 16:
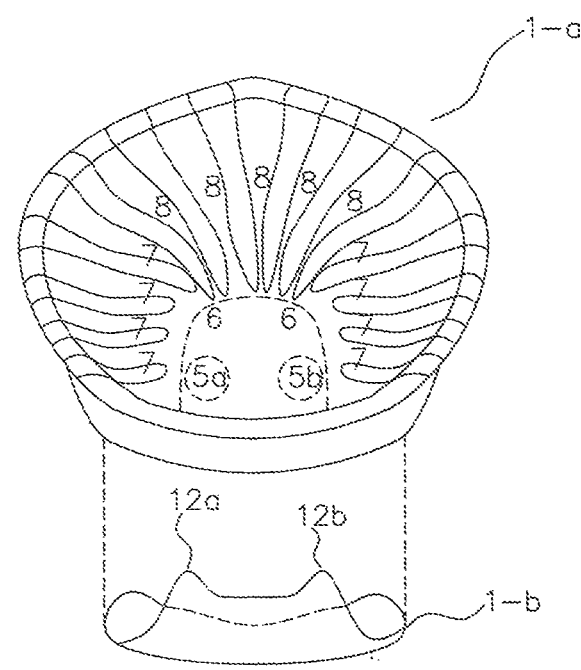
FIG. 16 is a schematic combined view of an alternative design of the AGP for bruxism, a "canine guidance anterior guidance" AGP.
Figure 16:
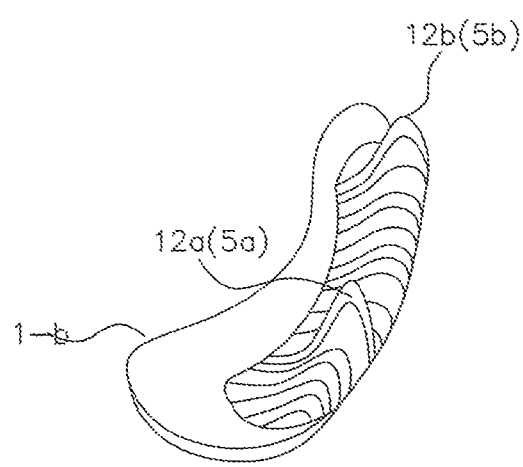
Figure 16A:
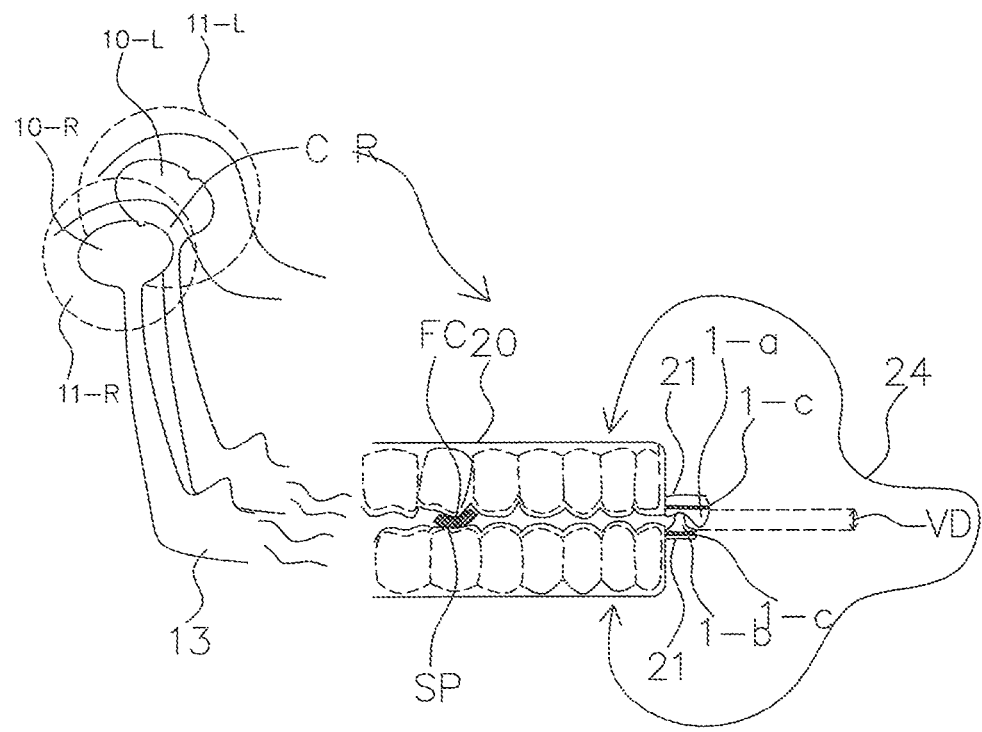

FIG. 16 is another example and a different design of a bruxism AGP (1), a "canine guidance" AGP (1), for a different version of a bruxism splint. There are two protrusions (12a and 12b) on the mandibular component (1-b) of the AGP (1) that are spaced laterally apart in a way that would mimic ideal human "canine" anterior guidance. In other words, the mandibular component of the AGP, which mimics ideal lower canines, functions against the maxillary component of the AGP, which mimics ideal maxillary teeth. This design is developed for patients whose particular interferences (malocclusion) can be more efficiently neutralized by anterior guidance focused upon lateral poles of the mandibular component of the AGP, as compared to a single pointed protrusion (12) of the mandibular component (1b) of FIG. 11, when a patient wears the splint (1-4) and bruxes. The maxillary component (1-a) of the AGP (1) would be modified accordingly to provide three-dimensional guidance and limits to the mandible according to canine guidance when the patient bruxes. The overall shape of the maxillary component (1-a) of the AGP (1) is including, but not limited to, a smoothly rounded square, smoothly rounded oval, smoothly rounded pentagonal, smoothly rounded hexagonal shape. The size of the maxillary component (1-a) is less than 50 mm by 50 mm dependent upon the full range of motion and border limits of the mandible both horizontally and vertically for a particular patient.

In this example there are two areas of centric relation contact (5a) and (5b) on the posterior aspect of the flat area of the maxillary component (1-a) with a much broader area of long centric (6) on the anterior aspect of the flat area of the maxillary component (1a).

When the patient moves his mandible in laterotrusion to the left, only the left protrusion (12b) will be in contact.

As the patient moves his mandible back to centric relation the right protrusion (12a) moves back into contact simultaneous with the left protrusion (12b).

As the patient moves his mandible in laterotrusion to the right from centric relation only the right protrusion (12a) will be in contact with the maxillary aspect of the AGP (1-a). Within the full range of motion of the TMJs (11R and 11L) of the mandible (13), both protrusions (12a and 12b) of the mandibular component (1b) of the AGP (1) will be in contact in centric relation (CR) with the maxillary component (1a) of the AGP (1) at points (5a) and (5b), or long centric area (6) or one or the other protrusions (12a or 12b) will be in contact with an inclined plane, lateral guidance (7), which locate on the lateral aspects of the inclined plane, or protrusive guidance (8), which locates on the anterior aspect of the inclined plane, of the maxillary component (1-a) of the AGP (1) to provide appropriate anterior "canine" guidance to avoid posterior interferences, eliminate engrams, reduce the force of the muscles of mastication, and to allow freedom to the condyles (10-R and 10-L) of the TMJ's (11-R and 11-L) to be in their best stress bearing positions regardless the patient's individual occlusion or malocclusion.

This is all done with a minimal vertical dimension (VD) penalty, preferably less than 5 mm, when the patient is at rest as compared to all previous systems because the elimination of posterior interferences is accomplished with true three-dimensional guidance displacing the mandible inferiorly in excursions from centric relation. An excursion would be a movement of the mandible left, right or protrusively from the hinge axis of centric relation. From the hinge axis of centric relation, or another point or axis of the operators choosing, the three dimensional guidance of FIGS. 16 through 20 of the AGP provides anterior guidance and eliminates the interferences of all excursions to the full border limits of the mandible. And furthermore, the guidance of the AGP (1) may be placed anterior to the anterior teeth so the physical material for that guidance (AGP) is not developed on a splint at a position in between maxillary and mandibular anterior teeth, but rather independent of the position of anterior teeth and could be anterior to anterior teeth. FIG. 16-a is a perspective cross-sectional view of the mandible hinging up in centric relation indexing a bruxism AGP for a patient with or without a complex malocclusion onto the retentive pieces when the mandible is in centric relation and the vertical dimension is appropriate according to the first contact.

FIG. 16-b is a perspective view of the special retentive piece (20) of the current invention for the maxilla, the mandible, or both. The special retentive piece (20) for the maxilla, the mandible, or both has a shelf (21) to receive the appropriate respective component of the AGP (Anterior Guidance Package). The shelf (21) is located on the most anterior side of the retentive piece (20) and the open side of the groove (22) is oriented toward the apical aspect of the teeth when a patient has a special retentive piece (20) adapted to the maxillary arch, or the mandibular arch or both arches. The special retentive piece (20) of the current application is moldable, retentive, stiff, and thin. The special retentive piece (20) can be used for both the maxillary and mandibular retentive pieces to place the AGP (1) anterior to the front teeth to comprise a splint (24) that is a combination of the special retentive pieces (20) and the AGP (1).

One major advantage to be gained by this characteristic of the AGP (1), as shown in FIG. 16-a, is the ability to place the AGP (1), and therefore the anterior guidance anywhere on the retentive pieces to include the shelf (21). The AGP provides all the guidance independent of teeth so it may be placed anywhere transversely (horizontally) or laterally. An example of a benefit of this characteristic of the AGP is the ability to place the AGP further forward (anterior) than where the anterior teeth are located.

This strategy can increase the mechanical advantage of the AGP (1) and therefore guidance over the muscles of mastication in contrast to any previous system.

This guidance can be provided no matter the condition or even presence of teeth because the AGP only requires the retentive piece stay on the arch as a foundation for the AGP and the guidance may be placed anterior to the traditional limitations of guidance with the help of the special retention piece (20) equipped with a height adjustable shelf (21) shown in FIG. 16-b. There is increased advantage over the muscles of mastication as compared to any previous system.

Figure 17:
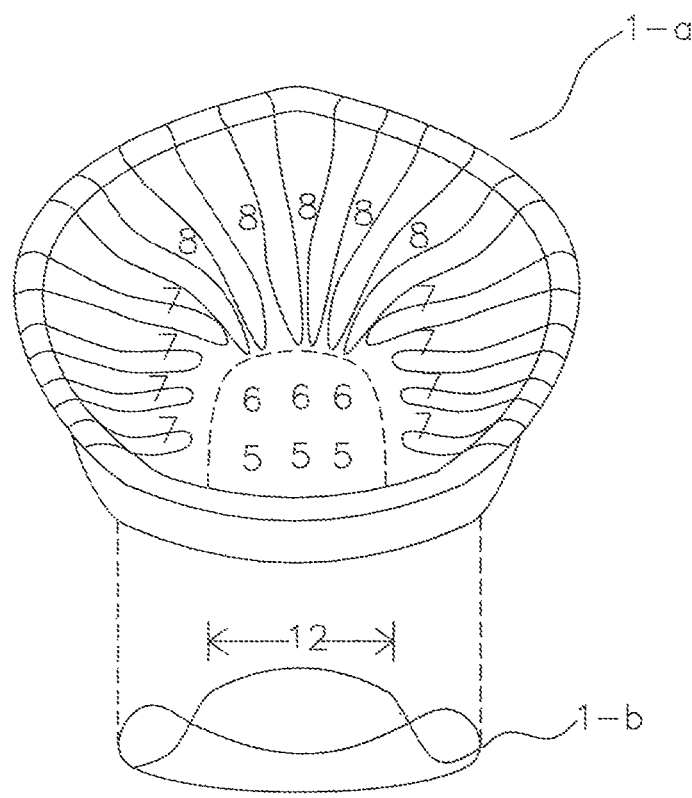
FIG. 17 is a schematic combined view of an alternative design of the AGP for bruxism, a "group function anterior guidance" AGP.
Figure 17:
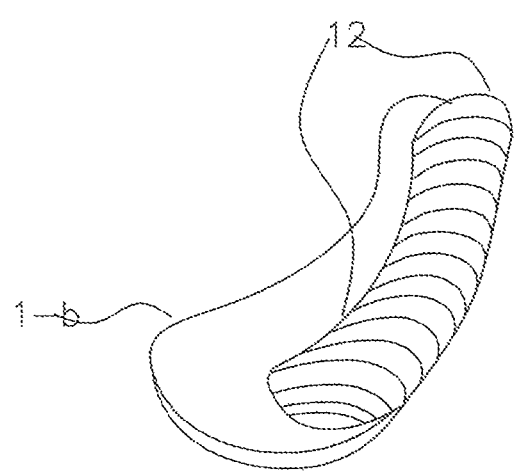

FIG. 17 is another example and a different design of a bruxism AGP (1), a "group function anterior guidance" AGP (1), which is created for a different version of a bruxism splint. There is a very broad protrusion (12) on the mandibular component (1-b) of the AGP (1) that would mimic group function from canine to canine, or premolar to premolar (or whatever the operator chooses) in a way that would mimic ideal human group function anterior guidance. This broadness of protrusion (12) can be accentuated anterior-posteriorly and/or laterally to give freedom to the mandible or set limits to the mandible according to the treatment goals of the operator.

This design is developed for patients whose particular interferences (malocclusion) can be more efficiently neutralized by anterior guidance that is broad from the left anterior lateral pole to the right anterior lateral pole of the mandibular component of the AGP, as compared to a single pointed protrusion (12) of the mandibular component (1b) of FIG. 11, when a patient wears the splint (1-4) and bruxes.

The maxillary component (1-a) of the AGP (1) would be modified according to group function guidance when the patient bruxes.

The overall shape of the maxillary component (1-a) of the AGP (1) is including, but not limited to, a smoothly rounded square, smoothly rounded oval, smoothly rounded pentagonal, smoothly rounded hexagonal shape. The size of the maxillary component (1-a) is less than 50 mm by 50 mm dependent upon the full range of motion and border limits of the mandible both horizontally and vertically for a particular patient.

There will be a broad area of centric relation stop (5), which is broader, in contrast to a centric relation stop (5) of a maxillary component that is coupled to a single pole protrusion (12), and locates on the posterior aspect of the flat area of the maxillary component, and a broad area of long centric (6), which is broader, in contrast to an area of long centric (6) in a maxillary component which is coupled to a single pole protrusion (12), and locates on the anterior aspect of the flat area of the maxillary component.

As with any AGP (1) construction, the steepness and depth of the areas of lateral and protrusive guidance on the maxillary component (1-a) of the AGP (1) can also be controlled to provide anterior stops and guidance to the mandible for whatever treatment goals the operator has in mind.

As with any AGP (1) construction, the steepness and depth of the protrusion (12) or protrusions (12a and 12b) of the mandibular component (1-b) of the AGP (1) can also be controlled to provide anterior stops and guidance to the mandible for whatever treatment goals the operator has in mind. Within the full range of motion of the TMJ's (11-R and 11-L) of the mandible (13) the broad protrusion (12) of the mandibular component (1-b) of the AGP (1) will be in contact in centric relation (5) with the maxillary aspect (1-a) of the AGP (1) or long centric area (6) or a lateral aspect of the broad protrusion (12) will be in contact with an inclined plane, lateral guidance (7), which locate on both lateral aspects of the inclined plane, or protrusive guidance (8), which locates on the anterior aspect of the inclined plane of the maxillary component (1a) of the AGP (1) to provide appropriate anterior "group function" guidance to avoid posterior interferences, eliminate engrams, reduce the force of the muscles of mastication, and to allow freedom to the condyles (10-R and 10-L) of the TMJs (11-R and 11-L) to be in their best stress bearing positions.

This is all done with a minimal vertical dimension (VD) penalty, preferably less than 5 mm, when the patient is at rest as compared to all previous systems because the elimination of posterior interferences is accomplished with true three-dimensional guidance displacing the mandible inferiorly in excursions from centric relation. And furthermore, the guidance of the AGP (1) may be placed anterior to the teeth so the physical material for that guidance is not in addition, but independent of and anterior to anterior teeth. This guidance can be provided no matter the condition or even presence of teeth and because the guidance may be placed anterior to the traditional limitations of guidance, there is increased advantage over the muscles of mastication as compared to any previous system.

Figure 18:
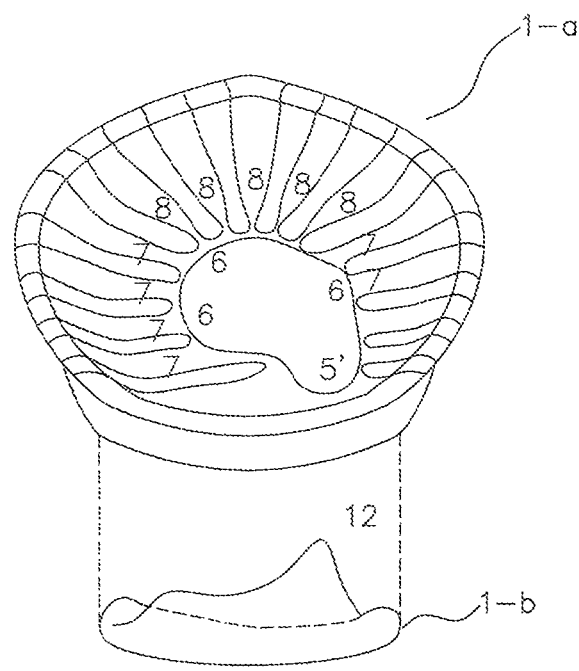
FIG. 18 is a schematic combined view of an alternative design of an AGP to treat TMD, an "asymmetric TMD treatment" AGP.
Figure 18:
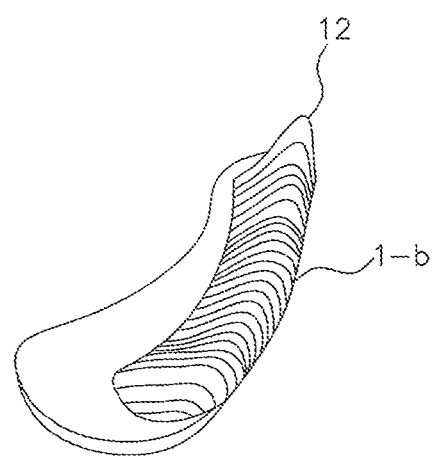

FIG. 18 is an example of TMD (Temporo Mandibular Disorder) treatment AGP (1), an "asymmetric TMD treatment" AGP (1) to enable a clinician to treat a mandible that has had damage to one TMJ, or the muscles, ligaments, or tendons of mastication unilaterally, or other clinical problems in which the operator needs the ability to control the movements and limits of the front end of the mandible asymmetrically. This is a very different clinical application of the AGP (1). The design of this AGP (1) reflects the operators' prescription to apply very different guidance and limits to each TMJ (11-R and 11-L) independently.

In this example the protrusion (12) is located laterally to the midline. The asymmetrical depth and steepness of both the mandibular aspect (1-b) and the maxillary aspect (1-a) of the AGP (1) can be controlled to provide anterior stops, limits and guidance for the treatment goals of the operator in this case asymmetrically providing very different parameters to each TMJ (11-R and 11-L). In this circumstance the patients' mandible (13) upon closing is guided into a position of rest (5'), which is other than centric relation that is proscribed by the operator for each patient's particular malady or damage. From this designated position of rest (5') the three-dimensional guidance to long centric (6) which has a customized shape, which is designed based on the damage of each patient on the anterior aspect of the flat area of the maxillary component, to provide guidance for this particular damage profile and then further to lateral guidance (7), which locate on both lateral aspects of the inclined plane of the maxillary guidance component, and protrusive guidance (8), which locates on the anterior aspect of the inclined plane of the maxillary guidance component, provide an asymmetrical protection and therapy for the particular damage or malady of each patient.

Figure 19:
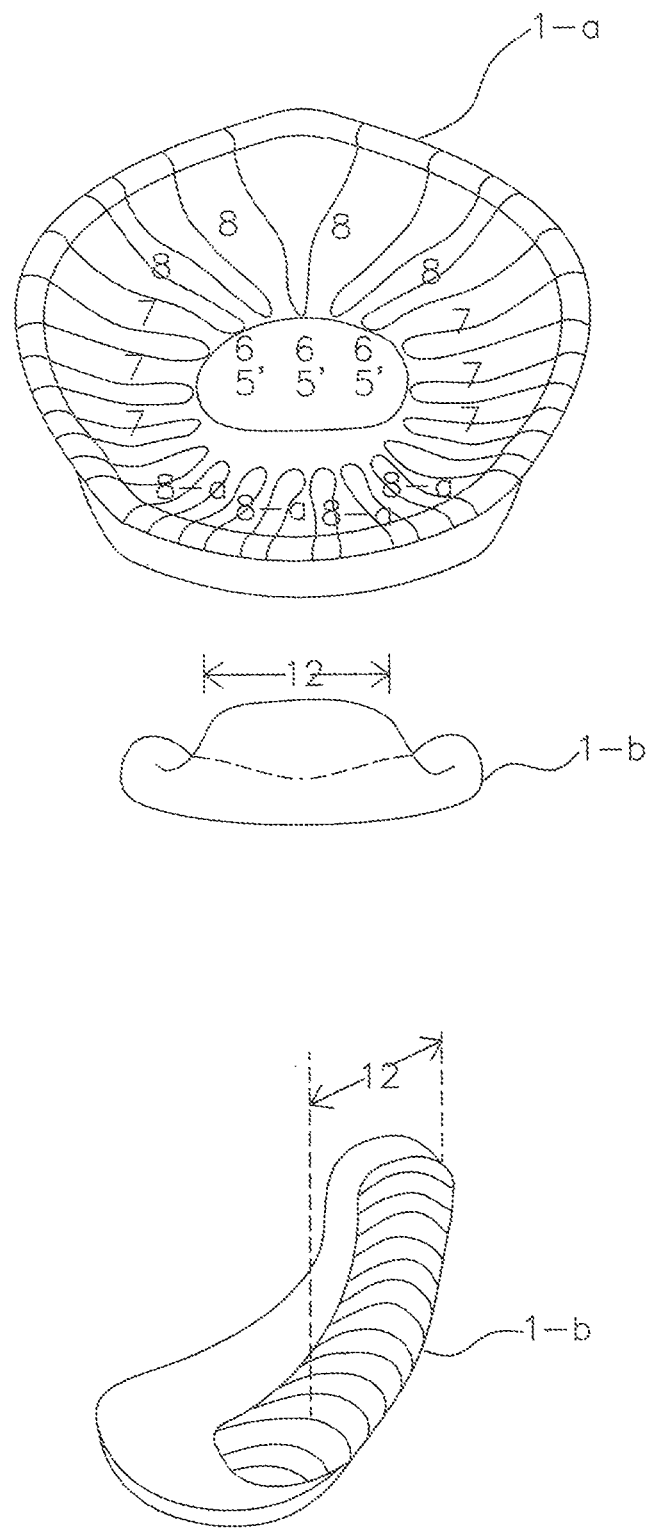
FIG. 19 is a schematic combined view of an alternative design of an AGP to treat TMD, an "a bilateral anterior repositioning TMD treatment" AGP.

FIG. 19 is another example of a TMD treatment AGP (1), a "bilateral anterior repositioning TMD treatment" (sometimes called a REPO) AGP (1) to enable a clinician to make an anterior repositioning splint to treat bilateral anterior disc displacement of the TMJ's. Again, a very different clinical application of the AGP (1) and a further example of the flexibility of treatments the AGP (1) can provide to a clinician with its ability to provide three-dimensional control of the front end of the mandible.

In this circumstance, both the mandibular aspect of the AGP (1-b) and the maxillary aspect of the AGP (1-a) are modified so that as the patient closes his mandible (13), it is guided forward and vertically to the designated position of rest (5') customized to treat the patients' damage in which both the condyles (10-R and 10-L) of the TMJ's (11-R and 11-L) recapture both the discs bilaterally.

The maxillary aspect of the AGP (1-a) has customized protrusive guidance (8a) located on the posterior aspect of the maxillary component, where otherwise would be the centric relation position (posterior aspect of the maxillary component (1-a); position 5), that guides the mandible protrusively and vertically to this therapeutic position of rest (5'). The position of rest (5') is designated based on the damage of each patient.

From this designated position of rest (5') that has recaptured both discs of the TMJ's, the three-dimensional guidance for the mandible to long centric area (6), on the anterior aspect of the flat area, and then further to lateral guidance (7), which locate on both lateral aspects of the inclined plane of the maxillary guidance component, and protrusive guidance (8), which locate on the anterior aspect of the inclined plane of the maxillary guidance component, provide symmetrical protection and therapy for the particular damage or malady each patient exhibits, elimination of posterior interferences, elimination of engrams, and the reduction of the forces of the muscles of mastication. This is all done with a minimal vertical dimension (VD) penalty when the patient is at rest as compared to all previous systems because the anterior repositioning of the condyles (10-R and 10-L) and the elimination of posterior interferences is accomplished with true three-dimensional guidance displacing the mandible (13) vertically in the therapeutic movement to reposition the condyles (10-R and 10-L) and the excursions from this designated position (5'). And furthermore, the guidance of the AGP (1) may be placed anterior to the teeth so the physical material for that guidance is not in addition, but independent of and anterior to anterior teeth.

This guidance can be provided no matter the condition or even presence of teeth and because the guidance may be placed anterior to the traditional limitations of guidance where there is increased advantage over the muscles of mastication as compared to any previous system.

A series of AGPs could be designed by the operator to gently "walk back" the condyles to centric relation as the posterior tissues are healed.

Figure 20:
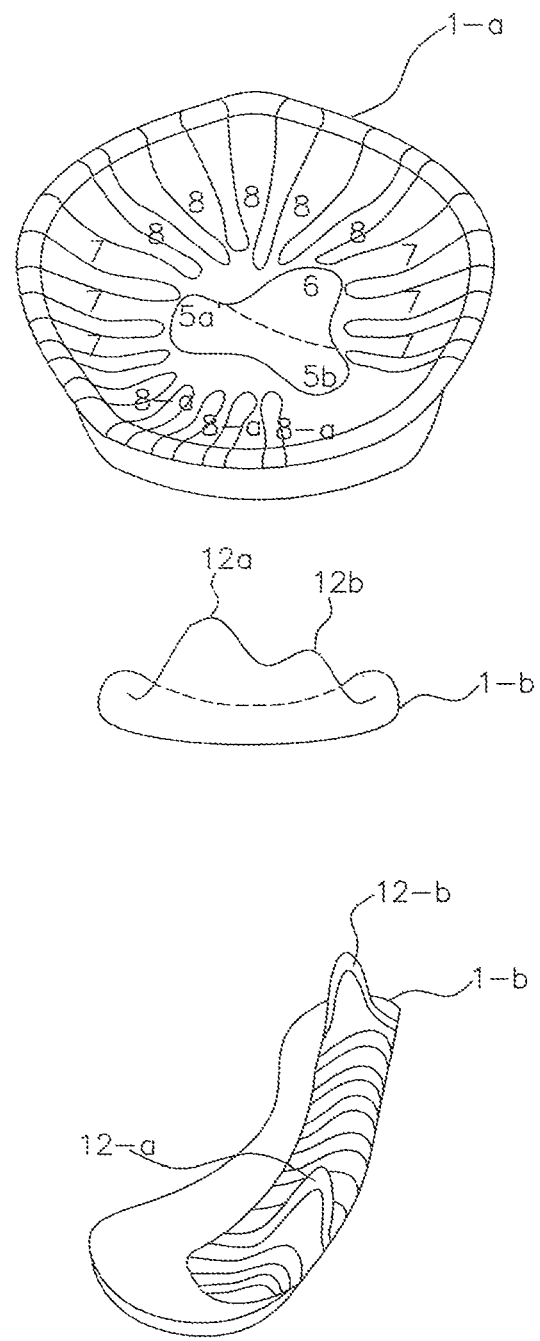
FIG. 20 is a schematic combined view of an alternative design of an AGP to treat TMD, an "a unilateral anterior repositioning TMD treatment" AGP.

FIG. 20 is another example of a TMD treatment AGP (1), a "unilateral anterior repositioning splint" AGP (1) to enable a clinician to create a TMD treatment appliance which can be selective and differential to each TMJ (11-R and 11-L) or other unilateral maladies of the mandible (13), or supporting structures. Again, this is another example of a very different clinical application, taking advantage of the robust flexibility of the AGP (1).

In this circumstance, the patient has an anteriorly displaced meniscus in the right TMJ (11-R), and the left TMJ (11-L) is normal. The clinician proscribes an AGP that anteriorly repositions the right TMJ (11-R) to recapture the displaced meniscus, but allows the left TMJ (11-L) to be in centric relation.

On the mandibular aspect of the AGP (1-b) there are two protrusions (12a and 12b) in which the protrusion on the right (12a) is taller and steeper than the protrusion on the left (12b).

The maxillary aspect (1-a) of the AGP (1) is modified accordingly. The right area of anterior repositioning (5a'), that recaptures the anteriorly displaced disc of the right TMJ, is located anteriorly and has a deeper indentation that is located anteriorly on the right aspect of the flat area of the maxillary component, and has customized anterior protrusive guidance (8a), posterior to the proscribed area of rest (5a') in contrast to the position of rest (5b), which locates on the left posterior aspect of the flat area of the maxillary component, to enable the operator to anteriorly reposition the right condyle (10-R) while allowing the left condyle (10-L) to assume centric relation at rest.

In this circumstance, as the patient closes his mandible (13) the right condyle (10-R) is guided anteriorly and vertically by the broader and taller right protrusion (12a) of the mandibular aspect (1b) of the AGP (1) into the deeper and broader area (5a') of the maxillary aspect (1a) of the AGP (1) to recapture the displaced disc of the right TMJ (11-R).

The left condyle (10-L) of the left TMJ (11-L) is guided into its centric relation position by the left protrusion (12b) of the mandibular aspect (1 b) of the AGP (1) into the centric relation position (5b) of the maxillary aspect (1a) of the AGP (1). (Please refer FIG. 7 and FIG. 20)

From this therapeutically designated position of rest (5a' and 5b), based on the patients' damage profile, that has recaptured the right disc of the right TMJ (11-R), the three-dimensional guidance to long centric rest (6) and then further to lateral guidance (7), and protrusive guidance (8), provide asymmetrical protection and therapy for the particular damage or malady this patient exhibits, elimination of posterior interferences, elimination of engrams, and the reduction of the forces of the muscles of mastication.

This is all done with a minimal vertical dimension (VD) penalty when the patient is at rest as compared to all previous systems because the anterior repositioning of the right condyle (10-R) and the elimination of posterior interferences is accomplished with true three-dimensional guidance displacing the mandible (13) vertically in the therapeutic movement to reposition the right condyle (10-R) and the excursions from this designated therapeutic position. And furthermore, the guidance of the AGP (1) may be placed anterior to the teeth so the physical material for that guidance is not in addition, but independent of and anterior to anterior teeth. This guidance can be provided no matter the condition or even presence of teeth and because the guidance may be placed anterior to the traditional limitations of guidance there can be increased advantage over the muscles of mastication as compared to any previous system.

The AGP (1) of the current application enables an operator to control the patients mandible upon closing to arrive at whatever destination the operator chooses using whatever route the operator chooses. These examples of the AGP (1) illustrate the robust flexibility of the AGP (1) to enable an operator to create treatment strategies for a wide range of maladies or combinations of maladies in which three-dimensional control can be applied to the anterior of the mandible in ways never imagined before. The pre-fabricated AGP (1) of the current invention can be made in many different shapes and sizes based on the diagnosis, malocclusion, and treatment plan of the patient. Different styles of bruxism AGP's (1) can be created by changing the shape of the mandibular aspect of the AGP (1-b) from a single protrusion (12), to a broader wider protrusion (12) for a "group function" AGP (1), to two protrusions (12a and 12b) for a "canine guidance" AGP (1). The properties of guidance and limits of the maxillary aspect (1-a) of the AGP (1) are appropriately developed opposing these different shapes and sizes of mandibular aspects (1-b) to accomplish the treatment goals and style of bruxism appliance the operator proscribes. In the case of damage to the mouth, jaw, TMJ dysfunction, or internal derangement, an AGP (1) can be specifically designed to address these conditions or combinations of conditions using the AGP's (1) unique ability to provide three-dimensional control and limits for the front end of the mandible. For example, one could construct an AGP (1) with asymmetrical lateral guidance (7) and/or protrusive guidance (8). An AGP (1) of current invention could be constructed to anteriorly reposition the condyle of the TMJ bilaterally or unilaterally. The AGP (1) of current invention enables an operator to control the patients mandible when the patient closes to arrive at whatever destination the operator chooses using whatever route the operator chooses. This property of the AGP (1) is unique and enables myriad treatment strategies for a wide range of problems or combinations of problems. The AGP (1) can be indexed into an appliance coincident with centric relation position of a patients jaw or at some other position of the operators choosing dependent on the treatment goals for that patient. With the use of the CAD-CAM AGP, which was disclosed in another application by the inventor, a CAD-CAM AGP could be custom produced by an operator in an unprecedented way providing solutions to these conditions or combinations of conditions and at a significant lesser expense to both operator and patient.

The AGP (1) of the current application can be specifically produced that can move the mandible from the centric relation position into typical ideal guidance patterns for the treatment of bruxism or from a position other than centric relation into non-traditional guidance pathways for the treatment of specific TMJ treatment and other maladies. The AGP (1) of the current application can be utilized with alternative ways of determining what position other than centric relation position that the mandible should rest and be guided.

What is claimed is:

1. A pre-fabricated anterior guidance package (AGP) equipped dental device comprising:
a mandibular guidance component having a pair of upwardly extending protrusions, wherein each of the protrusions are laterally spaced apart on an anterior aspect of the mandibular guidance component and selectively positioned to align with canines of a human mouth; and
a maxillary guidance component having a concave bottom surface to movably contact the upwardly extending protrusions thereby providing anterior guidance to the mandibular guidance component about the upwardly extending protrusions, the concave bottom surface comprising a flat area and a curved area, wherein:
the flat area comprises a pair of centric relation contact regions proximate a posterior portion of the flat area and a long centric relation contact region proximate an anterior aspect of the flat area, each of the centric relation contact regions being configured to receive one of the protrusions of the mandibular guidance component,
the curved area comprises a plurality of lateral guidance contact points proximate two or more lateral aspects of the maxillary guidance component and a plurality of protrusive guidance contact points proximate one or more anterior aspects of the maxillary guidance component,
the upwardly extending protrusions are in contact with the bottom surface of the maxillary guidance component across lateral movement of temporo-mandibular joints of the mouth, and
the centric relation contact regions and guidance contact points guide movement of the upwardly extending protrusions of the mandibular guidance component so the AGP equipped dental device guides a mandible of the human mouth to avoid posterior interference in a substantially minimal stress bearing position.

2. The AGP equipped dental device of claim 1, wherein the protrusions comprises symmetrical left and right protrusions.

3. The AGP equipped dental device of claim 1, wherein left and right portions of the maxillary guidance component are symmetrical.

4. The AGP equipped dental device of claim 1, wherein the flat area is positioned proximate a mid-sagittal plane of the maxillary guidance component.

5. A pre-fabricated anterior guidance package (AGP) equipped dental device comprising:
a mandibular guidance component having a pair of upwardly extending protrusions, each upwardly extending protrusion being laterally spaced and selectively positioned to align with canines of a human mouth; and
a maxillary guidance component having a concave bottom surface to movably contact the upwardly extending protrusions thereby providing anterior guidance to the mandibular guidance component about the upwardly extending protrusions, the concave bottom surface comprising a bottom floor and one or more perimetral sidewalls, wherein the bottom floor comprises first and second index position contact regions, each index position contact region being configured to receive the one or more protrusions a respective protrusion of the mandibular guidance component to three-dimensionally control and guide the mandibular guidance component,
wherein the one or more sidewalls comprises a plurality of lateral guidance contact points proximate one or more lateral aspects of the maxillary guidance component and a plurality of protrusive guidance contact points proximate one or more anterior aspects of the maxillary guidance component,
wherein the upwardly extending protrusions are in contact with the bottom surface of the maxillary guidance component and index position contact regions across lateral movement of temporo-mandibular joints of the mouth; and
wherein the first and second index position contact regions, lateral contact points, and protrusive guidance contact points guide movement of the upwardly extending protrusions of the mandibular guidance component so the AGP equipped dental device guides a mandible of the human mouth to avoid posterior interference in a substantially minimal stress bearing position.

6. The AGP equipped dental device of claim 5, wherein the bottom floor comprises a bottommost area of the concave bottom surface of the maxillary guidance component.

7. The AGP equipped dental device of claim 5, wherein the bottom floor is substantially flat and at least one of the one or more sidewalls is curved.

8. The AGP equipped dental device of claim 5, wherein the protrusions comprises symmetrical left and right protrusions.

9. The AGP equipped dental device of claim 5, wherein left and right portions of the bottom floor are symmetrical.

10. A pre-fabricated anterior guidance package (AGP) for a dental device, the AGP comprising:
a mandibular guidance component having a pair of upwardly extending protrusions, each upwardly extending protrusion being laterally spaced and selectively positioned to align with canines of a human mouth; and
a maxillary guidance component having a concave bottom surface to movably contact the upwardly extending protrusions thereby providing anterior guidance to the mandibular guidance component about the upwardly extending protrusions, the concave bottom surface comprising at least two bottommost points and one or more curved perimetral sidewalls that extend along an anterior aspect and at least one lateral aspect of the maxillary guidance component,
wherein each of the bottommost points is configured to receive the respective protrusion of the mandibular guidance component,
wherein the one or more curved perimetral sidewalls is configured to three-dimensionally direct and guide each respective protrusion towards the bottommost points when the mandibular and maxillary guidance components mate wherein the upwardly extending protrusions are in contact with the bottom surface of the maxillary guidance component across lateral movement of temporo-mandibular joints of the mouth, and
wherein the bottom surface of the maxillary guidance components guides movement of the upwardly extending protrusions of the mandibular guidance component so the AGP equipped dental device guides a mandible of the human mouth to avoid posterior interference in a substantially minimal stress bearing position.

11. A pre-fabricated anterior guidance package (AGP) equipped dental device comprising:
- a mandibular guidance component having two upwardly extending protrusions that are laterally spaced apart, each upwardly extending protrusion being laterally spaced and selectively positioned to align with canines of a human mouth; and
- a maxillary guidance component having a concave bottom surface to movably contact the upwardly extending protrusions thereby providing anterior guidance to the mandibular guidance component about the upwardly extending protrusions, the concave bottom surface comprising a bottom floor and one or more curved sidewalls, wherein:
    - the bottom floor comprises two centric relation contact regions proximate a posterior portion of the bottom floor and a long centric relation contact region proximate an anterior aspect of the bottom floor, the two centric relation contact regions being configured to receive the two protrusions of the mandibular guidance component,
    - the one or more sidewalls comprises a plurality of lateral guidance contact points proximate left and right aspects of the maxillary guidance component and a plurality of protrusive guidance contact points proximate an anterior aspect of the maxillary guidance component,
    - the upwardly extending protrusions are in contact with the bottom surface of the maxillary guidance component, including the sidewalls and the bottom floor, across lateral movement of temporo-mandibular joints of the mouth, and
    - the contact regions, contact points, and protrusive guidance contact points guide movement of the upwardly extending protrusions of the mandibular guidance component so the AGP equipped dental device guides a mandible of the human mouth to avoid posterior interference in a substantially minimal stress bearing position.

12. The AGP equipped dental device of claim 11, wherein the two protrusions are laterally spaced apart to minimize stress and interference to the lower canines of the human mouth to provide canine guidance when the mandibular and maxillary guidance components mate.

* * * * *